(12) United States Patent
Grau-Campistany et al.

(10) Patent No.: US 12,011,499 B2
(45) Date of Patent: Jun. 18, 2024

(54) PEPTIDES AND COMPOSITIONS FOR USE IN COSMETICS

(71) Applicant: LIPOTRUE, S.L., Gava (ES)

(72) Inventors: Ariadna Grau-Campistany, Barcelona (ES); Silvia Pastor, Alicante (ES); Patricia Carulla, Barcelona (ES); Juan Carlos Escudero, Barcelona (ES)

(73) Assignee: LIPOTRUE, S.L., Gava (ES)

( * ) Notice: Subject to any disclaimer, the term of this patent is extended or adjusted under 35 U.S.C. 154(b) by 245 days.

(21) Appl. No.: 17/297,749

(22) PCT Filed: Jan. 3, 2020

(86) PCT No.: PCT/EP2020/050070
§ 371 (c)(1),
(2) Date: May 27, 2021

(87) PCT Pub. No.: WO2020/144109
PCT Pub. Date: Jul. 16, 2020

(65) Prior Publication Data
US 2022/0062145 A1    Mar. 3, 2022

(51) Int. Cl.
*A61K 38/00* (2006.01)
*A61K 8/64* (2006.01)
*A61Q 19/08* (2006.01)
*C07K 14/47* (2006.01)

(52) U.S. Cl.
CPC ............... *A61K 8/64* (2013.01); *A61Q 19/08* (2013.01); *C07K 14/47* (2013.01)

(58) Field of Classification Search
None
See application file for complete search history.

(56) References Cited

FOREIGN PATENT DOCUMENTS

| FR | 3052453 A1 | 12/2017 |
|---|---|---|
| KR | 20140074527 A | 6/2014 |
| WO | 2010091893 A1 | 8/2010 |

OTHER PUBLICATIONS

NCBI blast accessed on Aug. 4, 2023 at https://blast.ncbi.nlm.nih.gov/Blast.cgi#alnHdr_EMP29546 (Year: 2023).*
Smith et al. Proteoglycans in Normal and Healing Skin. Adv Wound Care (New Rochelle). Mar. 1, 2015; 4(3): 152-173 (Year: 2015).*
Martinez et al. Role of proteoglycans on skin ageing: a review. International Journal of Cosmetic Science, 2020, 42, 529-535 (Year: 2020).*
International Search Report and Written Opinion for corresponding application PCT/EP2020/050070 dated May 8, 2020.

* cited by examiner

*Primary Examiner* — Aradhana Sasan
*Assistant Examiner* — Mercy H Sabila
(74) *Attorney, Agent, or Firm* — LUCAS & MERCANTI, LLP

(57) ABSTRACT

A family of peptides which prevent and/or reduce the signs of skin aging (including chronological and/or environmental aging) and which are useful for skin firming; cosmetic compositions comprising peptides and cosmetic uses and methods of peptides or cosmetic compositions.

12 Claims, 8 Drawing Sheets

Specification includes a Sequence Listing.

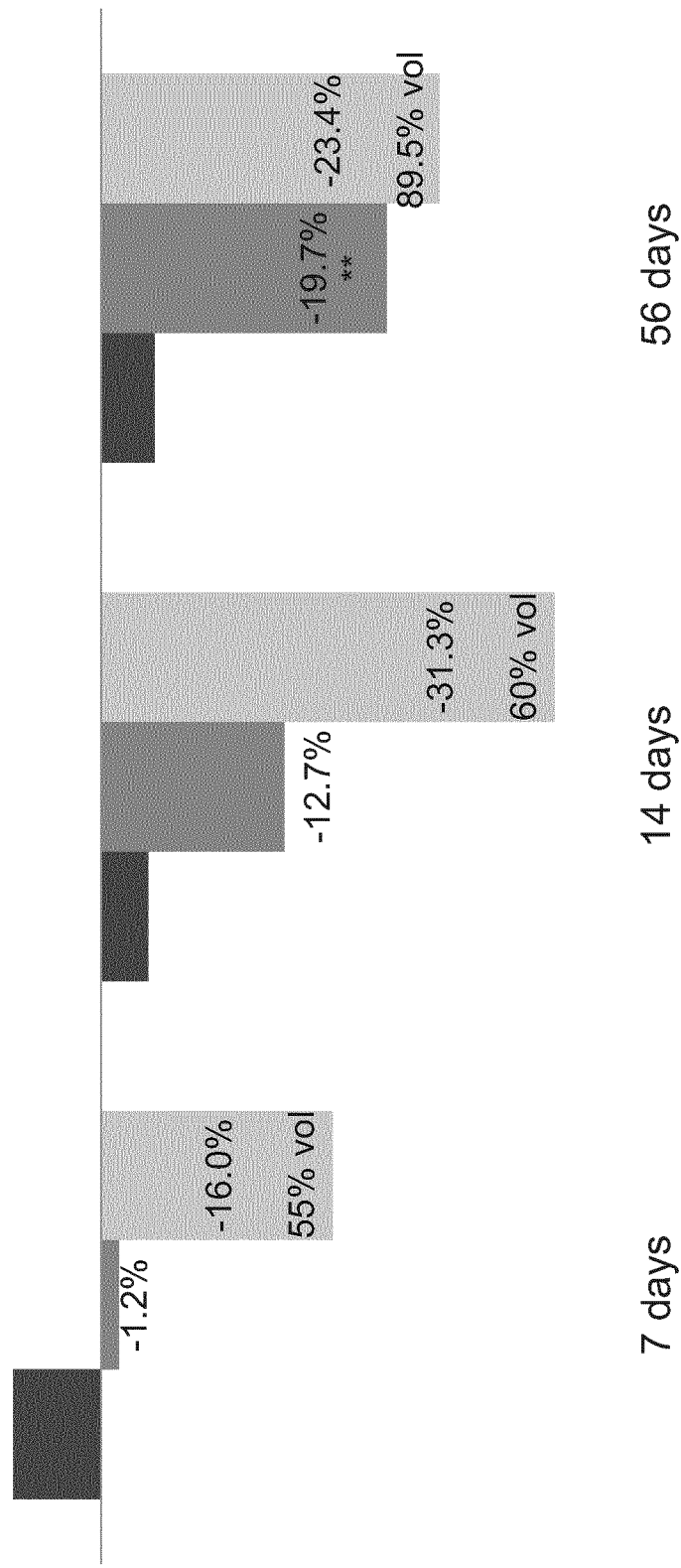

PEPTIDES AND COMPOSITIONS FOR USE IN COSMETICS

CROSS-REFERENCE TO RELATED APPLICATIONS

This application is a 371 of PCT/EP2020/050070, filed Jan. 3, 2020, which claims the benefit of European Patent Application No. 19382011.5 filed Jan. 8, 2019, each of which are incorporated herein by reference.

The present invention relates to the field of cosmetics, more precisely to peptides and compositions with firming and anti-aging activities and methods and uses thereof in the field of cosmetics.

In the last decades life expectancy of the population has increased significantly. In addition, there is also an increased concern in the population regarding personal aesthetics and to try to delay or minimize the appearance of signs related to aging.

The skin is the largest organ in humans and due to its location, in the body interface, is subject to intrinsic (chronologic) aging and extrinsic aging, the latter being caused by environmental factors (such as, for example, UV radiation, smoking or pollution). This continuous exposition and, obviously, aging, leads to changes in the skin and to the appearance of imperfections therein (for example, loss of firmness, wrinkling, roughness and/or sagginess).

One of the main constituents of the skin is the extracellular matrix (hereinafter, ECM).

It is widely known that the ECM is a complex mixture of secreted proteins, mainly, collagen and elastic fibres, which provide tensile strength and which are embedded in a viscoelastic gel comprising proteoglycans, glycoproteins (such as, fibronectin, laminin and tenascin) and water.

Said ECM is responsible for several of the physical properties of the skin as, for example, turgency, firmness and viscoelasticity. Hence, most of the signs of skin aging and loss of firmness thereof, are due to changes in the ECM of the skin (loss of structure or content or alterations thereof). As the skin ages, changes in skin thickness and in the quality of the dermis and epidermis are observed. The levels and the composition of glycosaminoglycans present in the ECM (among them we find, for example, hyaluronic acid), relevant for the water content and, hence, for the turgency of the skin, become progressively lower. This results in the skin being progressively drier and thinner. Other ECM constituents as, for example, collagen and elastic fibres, become disorganized and degraded. This general loss of integrity leads to skin rigidity and diminished elasticity (Farage M. A. and Miller K. W., *Structural characteristics of the ageing skin: a review* (2007) Cutaneous and ocular toxicology, 26, 343-357).

Proteoglycans are one of the main components of the ECM. All proteoglycans are characterized by a protein portion, called the core protein, and one or more unbranched, long and negatively charged polysaccharide chains called glycosaminoglycans (hereinafter, GAG) which are covalently attached to the core protein. Depending on the GAG chain, proteoglycans are categorised as heparan sulphate proteoglycans (for example, perlecan), chondroitin sulphate proteoglycans (for example, aggrecan), dermatan sulphate proteoglycans (for example, versican) and keratan sulphate proteoglycans (for example, lumican).

Among said proteoglycans, one that has shown to have a central role in the maintenance and functioning of the ECM is versican (Uniprot reference number: P13611 (CSPG2_HUMAN); SEQ ID NO: 1). Said protein is a large chondroitin sulphate proteoglycan, which is transcribed from a single gene localized on chromosome 5q 12-14 in the human genome and extends over 90 kb. The gene comprises 15 exons. Versican comprises at least four variants (V0, V1, V2 and V3) resulting from the alternative splicing of versican's mRNA.

All variants comprise an amino terminal G1 domain, which interacts with the glycosaminoglycan hyaluronan (for example, that present in the ECM), and a carboxyl terminal domain called G3 domain which comprises a C-type lectin binding domain, two epidermal growth factor repeats and a complement regulatory region. The difference between the four variants can be found in the core region, which contains the glycosaminoglycan binding domains. V0 contains the α and β domains, V1 the β domain, V2 the α domain and V3 none.

Given the above structure, versican has been shown to be, as already mentioned above, an important component of the ECM. It has a structural and biomechanical role, as it binds to hyaluronan, fibrillin-microfibrils and elastin, linking elastic fibres to the ground matter, but also a cell biological role influencing multiple cellular events such as cell migration and cell proliferation (Wight, T. N., *Versican: a versatile extracellular matrix proteoglycan in cell biology* (2002) Current Opinion in Cell Biology, 14: 617-623).

Other relevant molecules of the ECM are, as already mentioned above:

Elastic fibers: It is widely known that degradation of elastic fibres is a major contributing factor in aging, causing loss of elasticity, wrinkling, sagginess, and roughened texture of the skin. Regarding the components of elastic fibers it is important to note that tropoelastin is necessary for the formation of mature elastin while fibrillin-1 appears to be the major structural component of microfibrils where it acts as the scaffold for elastin deposition in adult tissues, and has key biomechanical and biochemical roles in the skin (Langton A. K., Sherratt M. J., Griffiths C. E. M. and Watson R. E. B., *A new wrinkle on old skin: the role of elastic fibres in skin ageing* (2010) International Journal of Cosmetic Science, 32, 330-339).

Hyaluronic acid: is a component of the ECM which has been shown to be related to hydration of the skin and, hence, the turgency thereof, as a result of its high water-retention capacity (Nemoto T., Kubota R., Murasawa Y. and Isogai Z., *Viscoelastic properties of the human dermis and other connective tissues and its relevance to tissue aging and aging-related diseases* (2012) Viscoelasticity—From Theory to Biological Applications, book edited by Juan de Vicente). Additionally, the interaction of hyaluronan with various binding proteins (hyaladherins such as proteoglycans, to state some) makes hyaluronic acid a key molecule to act on firmness and tightness of the skin, not only topically but also as a dermal filler (Weindl G., Schaller M., Schäfer-Korting M., Korting H. C., *Hyaluronic Acid in the Treatment and Prevention of Skin Diseases: Molecular, Biological, Pharmaceutical and Clinical Aspects* (2004) Skin Pharmacol Physiol, 17, 207-213).

In recent years, the number of active ingredients to improve signs of skin aging, such as loss of firmness, skin texture and wrinkling, has increased considerably. Examples of such active ingredients are retinoids, vitamins or botanical extracts (Bradley E. J., Griffiths C. E. M., Sherratt M. J., Bell M. and Watson R. E. B., *Over-the-counter anti-ageing topical agents and their ability to protect and repair photoaged skin* (2015) Maturitas, 80, 265-272).

In the case of retinoids, noteworthy is retinoic acid which is nowadays the 'gold-standard' for the induction of synthesis of several molecules of the ECM (for example, collagen, fibronectin or laminin; Varani J., Mitra R. S., Gibbs D., Phan S. H., Dixit V. M., Mitra R., Wang T., Siebert K. J., Nickoloff B. J., Voorhees J. J., *All-Trans Retinoic Acid Stimulates Growth and Extracellular Matrix Production in Growth-Inhibited Cultured Human Skin Fibroblasts* (1990) The Journal of Investigative Dermatology, 94, 717-723). Hence, retinoic acid has been considered one of the most powerful compounds to treat the signs of aging, as it can significantly improve the clinical appearance of facial wrinkles by up-regulating the transcription and synthesis of proteins of the ECM such as collagen and fibronectin, and the inhibition of matrix metalloproteinases (hereinafter, MMP) (Varani J., Mitra R. S., Gibbs D., Phan S. H., Dixit V. M., Mitra R., Wang T., Siebert K. J., Nickoloff B. J., Voorhees J. J., *All-Trans Retinoic Acid Stimulates Growth and Extracellular Matrix Production in Growth-Inhibited Cultured Human Skin Fibroblasts* (1990) The Journal of Investigative Dermatology, 94, 717-723). However, there are several drawbacks in the use of retinoic acid as, for example: retinoic acid has to be used cautiously as it can easily produce skin irritation and it is not recommended to combine retinoic acid and sun exposure. Another major concern when using retinoids is their instability, especially in the presence of oxygen and light (Sorg O., Antille C., Kaya G. and Saurat J-H., *Retinoids in cosmeceuticals* (2006) Dermatologic Therapy, 19, 289-296).

Antioxidants are also used in order to reduce the concentration of free radicals in the skin and, therefore, counteract collagen degradation. An example of said antioxidants is ascorbic acid (also known as Vitamin C). Ascorbic acid, in addition to its antioxidant effect, induces the synthesis of proteins from the ECM (collagen I and III and elastin) while promoting epidermal differentiation and inhibiting MMP1, among others. Unfortunately, ascorbic acid, is extremely unstable and undergoes oxidation especially at high temperatures, aerobic conditions, high pH and/or when exposed to light (Manela-Azulay M., Azulay V., Aguinaga F., Issa M. C., *Vitamins and other Antioxidants* (2017) Daily Routine in Cosmetic Dermatology, 1-13).

In addition to chemically synthesized compounds, a wide range of botanical extracts and plant derived compounds are found in the market with multiple applications, such as, for example, grape extracts which comprise resveratrol (an antioxidant); green tea which comprises polyphenols; or soy which comprises isoflavones. However, the in vivo efficacy and composition of these ingredients is not sufficiently scientifically validated.

Hyaluronic acid, due to its viscoelastic properties and its capacity to retain water, has also been used in the cosmetic industry to keep skin hydrated, maintain elasticity and treat wrinkles by improving the roughness or even used as a dermal filler. However, currently, hyaluronic acid, is obtained from several sources, such as rooster combs or bacterial extracts and, consequently, these products can contain impurities and need to be characterized thoroughly (Kogan G., Soltés L., Stern R. and Gemeiner P., *Hyaluronic acid: a natural biopolymer with a broad range of biomedical and industrial applications* (2007) Biotechnological Letters 29, 17-25).

On the other hand, peptides can also be incorporated in cosmetic formulas to improve the signs of skin aging. Bioactive peptides can imitate body's own molecules and influence processes such as collagen synthesis, with the advantage that they have much better tolerability and stability. In addition, a wide range of activities, chemistries and indications can be developed for them (Zhang L. and Falla T. J., *Cosmeceuticals and peptides* (2009) Clinics in dermatology, 27, 485-494).

Despite the extensive variety of compounds and/or extracts in the field, there is still the need for alternative compositions with novel mechanisms of action and which have an overall effect on the ECM (for example, acting on one or more components of said matrix) leading to an effect on the firmness of the skin, and which allow the prevention and/or reduction of the signs of skin aging (chronological and/or environmental aging), and improve viscoelasticity and firmness of the skin.

The inventors of the present invention, after extensive and exhaustive research, have surprisingly found small peptides of six amino acids derived from the signalling peptide sequence in the N-terminal region of versican (SEQ ID NO: 1), and derivatives or variations of said peptides, which show activities directly related with the maintenance and production of ECM (as demonstrated in the examples included below). Hence, said peptides of the present invention are useful for the prevention and/or reduction of signs of skin aging; and/or for skin firming.

The inventors have demonstrated that peptides with SEQ ID NO: 2 and 3 (belonging to the N-terminal region of versican, where the signalling peptide is located, more precisely, positions 21 to 26 and 20 to 25 of SEQ ID NO: 1, respectively) have important activities inhibiting elastase activity and inhibiting the production of metalloproteinases 1 and 3 (this is, inhibition of the degradation of ECM); and promoting the synthesis of versican, tropoelastin (secreted precursor of elastin), fibrillin-1 and hyaluronic acid (four of the main structural components of the ECM). In addition, said peptides show improved quality in the firmness of the skin. Hence, said peptides have firming and antiaging effects.

Therefore, said peptides, are useful in cosmetics to improve the viscoelastic and firming characteristics of the skin and, hence, are useful to prevent and/or reduce the signs of skin aging related with alterations or deficiencies in the ECM by directly acting in various aspects related with the structural integrity of the ECM.

Also within the scope of the present invention are the peptides which result from conservative substitutions in the above-mentioned peptides derived from versican (this is, peptides SEQ ID NO: 2 and SEQ ID NO: 3).

Therefore, in a first embodiment, the present invention refers to a group of peptides effective at improving viscoelastic and firming characteristics of the skin, as it is directly derivable from the experimental results included below. Therefore, said peptides are useful in preventing and/or reducing the signs of skin aging.

In a further embodiment, the present invention refers to a composition comprising one of the peptides of the present invention or a combination thereof.

In an additional embodiment, the present invention refers to the use as a cosmetic of the peptides or the cosmetic compositions of the present invention.

A further embodiment of the present invention refers to the cosmetic use of the peptides or the compositions of the present invention to improve viscoelastic and firming characteristics of the skin, hence, preventing and/or reducing the signs of skin aging.

In another embodiment, the present invention refers to a method to prevent and/or reduce the signs of skin aging in a subject, characterized in that it comprises the use of a peptide or a composition of the present invention.

In a final embodiment, the present invention refers to a method to improve viscoelastic and firming characteristics of the skin in a subject, characterized in that it comprises the use of a peptide or a composition of the present invention.

The term "non-cyclic aliphatic group" and its plural, as used herein, have the common meaning given in the state of the art to said terms. Therefore, these terms refer to, for example and not restricted to, linear or branched alkyl, alkenyl and alkynyl groups.

The term "alkyl group" and its plural, as used herein, refer to a saturated, linear or branched group, which has between 1 and 24, preferably between 1 and 16, more preferably between 1 and 14, even more preferably between 1 and 12, and even more preferably still between 1, 2, 3, 4, 5 or 6 carbon atoms and which is bound to the rest of the molecule by a simple bond, including, for example and not restricted to, methyl, ethyl, isopropyl, n-propyl, i-propyl, isobutyl, tert-butyl, n-butyl, sec-butyl, n-pentyl, n-hexyl, heptyl, octyl, decyl, dodecyl, lauryl, hexadecyl, octadecyl, amyl, 2-ethylhexyl, 2-methylbutyl, 5-methylhexyl and similar. The alkyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "alkenyl group" and its plural, as used herein, refer to a linear or branched group which has between 2 and 24, preferably between 2 and 16, more preferably between 2 and 14, even more preferably between 2 and 12, even more preferably still 2, 3, 4, 5 or 6 carbon atoms, with one or more carbon-carbon double bonds, preferably with 1, 2 or 3 carbon-carbon double bonds, conjugated or unconjugated, which is bound to the rest of the molecule through a single bond, including, for example and not restricted to, the vinyl, oleyl, linoleyl and similar groups. The alkenyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "alkynyl group" and its plural, as used herein, refer to a linear or branched group which has between 2 and 24, preferably between 2 and 16, more preferably between 2 and 14, even more preferably between 2 and 12, even more preferably still 2, 3, 4, 5 or 6 carbon atoms, with one or more carbon-carbon triple bonds, preferably with 1, 2 or 3 carbon-carbon triple bonds, conjugated or unconjugated, which is bound to the rest of the molecule through a single bond, including, for example and not restricted to, the ethinyl group, 1-propinyl, 2-propinyl, 1-butinyl, 2-butinyl, 3-butinyl, pentinyl, such as 1-pentinyl and similar groups. The alkynyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "alicyclic group" and its plural, as used herein, have the common meaning given in the state of the art to said terms. Hence, these terms are used to refer to, for example and not restricted to, cycloalkyl or cycloalkenyl or cycloalkynyl groups.

The term "cycloalkyl" and its plural, as used herein, refer to a saturated mono- or polycyclic aliphatic group which has between 3 and 24, preferably between 3 and 16, more preferably between 3 and 14, even more preferably between 3 and 12, even more preferably still 3, 4, 5 or 6 carbon atoms and which is bound to the rest of the molecule through a single bond, including, for example and not limited to, cyclopropyl, cyclobutyl, cyclopentyl, cyclohexyl, cycloheptyl, methyl cyclohexyl, dimethyl cyclohexyl, octahydroindene, decahydronaphthalene, dodecahydro-phenalene, adamantyl and similar, and that can optionally be substituted by one or more groups, such as, alkyl, halo, hydroxy, alkoxy, carboxy, carbonyl, cyano, acyl, alkoxy-carbonyl, amino, nitro, mercapto and alkoxythio.

The term "cycloalkenyl" and its plural, as used herein, refer to a non-aromatic mono- or polycyclic aliphatic group which has between 5 and 24, preferably between 5 and 16, more preferably between 5 and 14, even more preferably between 5 and 12, even more preferably still 5 or 6 carbon atoms, with one or more carbon-carbon double bonds, preferably with 1, 2 or 3 carbon-carbon double bonds, conjugated or unconjugated, which is bound to the rest of the molecule through a single bond, including, for example and not restricted to, the cyclopent-1-en-1-yl group and similar groups, and that can optionally be substituted by one or more groups, such as, alkyl, halo, hydroxy, alkoxy, carboxy, carbonyl, cyano, acyl, alkoxy-carbonyl, amino, nitro, mercapto and alkoxythio.

The term "cycloalkynyl" and its plural, as used herein, refer to a non-aromatic mono- or polycyclic aliphatic group which has between 8 and 24, preferably between 8 and 16, more preferably between 8 and 14, even more preferably between 8 and 12, even more preferably still 8 or 9 carbon atoms, with one or more carbon-carbon triple bonds, preferably with 1, 2 or 3 carbon-carbon triple bonds, conjugated or unconjugated, which is bound to the rest of the molecule through a single bond, including, for example and not restricted to, the cyclooct-2-yn-1-yl group and similar, and that can optionally be substituted by one or more groups, such as, alkyl, halo, hydroxy, alkoxy, carboxy, carbonyl, cyano, acyl, alkoxy-carbonyl, amino, nitro, mercapto and alkoxythio.

The term "aryl group" and its plural, as used herein, refer to an aromatic group which has between 6 and 30, preferably between 6 and 18, more preferably between 6 and 10, even more preferably 6 or 10 carbon atoms, which comprises 1, 2, 3 or 4 aromatic rings, bound by a carbon-carbon bond or fused, and which is bound to the rest of the molecule through a single bond, including, for example and not restricted to, phenyl, naphthyl, diphenyl, indenyl, phenanthryl or anthranyl among others. The aryl group can be optionally substituted by one or more substituents, such as, halo, hydroxy, alkoxy, carboxy, carbonyl, cyano, acyl, alkoxy-carbonyl, amino, nitro, mercapto and alkoxythio.

The term "aralkyl group" and its plural, as used herein, refer to an alkyl group substituted by an aromatic group, with between 7 and 24 carbon atoms and including, for example and not restricted to, —(CH$_2$)1-6-phenyl, —(CH$_2$)1-6-(1-naphtyl), —(CH$_2$)1-6-(2-naphtyl), —(CH$_2$)1-6-CH(phenyl)$_2$ and similar. The aralkyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "heterocyclic group" and its plural, as used herein, refer to a 3-10 member heterocycyl or hydrocarbon ring, in which one or more of the ring atoms, preferably 1, 2 or 3 of the ring atoms, is a different element to carbon, such as nitrogen, oxygen or sulfur and may be saturated or unsaturated. For the purposes of this invention, the heterocyclyl can be a cyclic, monocyclic, bicyclic or tricyclic system which may include fused ring systems; and the nitrogen, carbon or sulfur atoms can be optionally oxidized in the heterocyclyl radical; the nitrogen atom can optionally be quaternized; and the heterocyclyl radical may be partially or completely saturated or may be aromatic. With increasing preference, the term heterocyclic relates to a 5 or 6-member ring. The heterocyclic groups can be optionally substituted by one or more substituents, such as, halo, hydroxy, alkoxy, carboxy, carbonyl, cyano, acyl, alkoxy-carbonyl, amino, nitro, mercapto and alkoxythio.

The term "heteroarylalkyl group" and its plural, as used herein, refer to an alkyl group substituted with a substituted or unsubstituted aromatic heterocyclyl group, the alkyl group having from 1 to 6 carbon atoms and the aromatic heterocyclyl group between 2 and 24 carbon atoms and from 1 to 3 atoms other than carbon and including, for example and not restricted to, —($CH_2$)1-6-imidazolyl, —($CH_2$)1-6-triazolyl, —($CH_2$)1-6-thienyl, —($CH_2$)1-6-furyl, —($CH_2$)1-6-pyrrolidinyl and similar. The heteroarylalkyl groups can be optionally substituted by one or more substituents, such as, halo, hydroxy, alkoxy, carboxy, carbonyl, cyano, acyl, alkoxy-carbonyl, amino, nitro, mercapto and alkoxythio.

The terms "halo" or "halogen", as used in the present document, refer to fluorine, chlorine, bromine or iodine, and its anions are referred to as halides.

As used herein, the term "derivative" and its plural, refer both to cosmetically acceptable compounds, this is, derived from the compound of interest that can be used in the preparation of a cosmetic, and to cosmetically unacceptable derivatives since these may be useful in the preparation of cosmetically acceptable derivatives.

As used in the present document, the term "salt" and its plurals refer to any type of salt from among those known in the state of the art, for example, halide salts, hydroxy acid salts (such as oxyacid salts, acid salts, basic salts and double salts), hydroxo salts, mixed salts, oxy salts or other hydrated salts. This term comprises both cosmetically acceptable salts and cosmetically unacceptable salts, since the latter may be useful in the preparation of cosmetically acceptable salts.

As used in the present document, the term "isomer" and its plural refer to optical isomers, enantiomers, stereoisomers or diastereoisomers. The individual enantiomers or diastereoisomers, as well as their mixtures, may be separated by conventional techniques known in the state of the art.

As used herein, the term "solvate" and its plural refer to any solvate known in the state of the art, such as polar, apolar or amphiphilic solvates, and include any cosmetically acceptable solvate which, when administered or applied to the interested subject (directly or indirectly) provides the compound of interest (the peptide or peptides of the present invention). Preferably, the solvate is a hydrate, a solvate with an alcohol such as methanol, ethanol, propanol or isopropanol, a solvate with an ester such as ethyl acetate, a solvate with an ether such as methyl ether, ethyl ether or THF (tetrahydrofuran) or a solvate with DMF (dimethylformamide), and more preferably a hydrate or a solvate with an alcohol such as ethanol.

In addition, as used herein, the term "amino acid" and its plural include the amino acids codified by the genetic code as well as uncodified amino acids, whether they are natural or not and whether they are D- and L-amino acids. Examples of uncodified amino acids are, without restriction, citrulline, ornithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4 aminobenzoic acid, 4-chlorophenylalanine, 2,3-diaminopropionic acid, 2,4 diaminobutyric acid, cycloserine, carnitine, cysteine, penicillamine, pyroglutamic acid, thienylalanine, hydroxyproline, allo-isoleucine, allo-threonine, isonipecotic acid, isoserine, phenylglycine, statin, β-alanine, norleucine, N-methylamino acids, α-amino acids and β-amino acids, among others, as well as their derivatives. Nevertheless, further unnatural amino acids are known in the state of the art (see, for example, "*Unusual amino acids in peptide synthesis*" by D. C. Roberts and F. Vellaccio, The Peptides, Vol. 5 (1983), Chapter VI, Gross E. and Meienhofer J., Eds., Academic Press, New York, USA).

The "percentage of identity" regarding peptides, polypeptides and proteins, as used herein, has the meaning commonly attributed in the state of the art and, hence, relates to the percentage of amino acids which are identical between two amino acid sequences which are compared after an optimal alignment of these sequences, where said percentage is merely statistical and the differences between the two amino acid sequences are randomly distributed throughout the sequence. "Optimal alignment" is understood as that alignment of amino acid sequences giving rise to a greater percentage of identity. The percentage of identity is calculated by determining the number of identical positions in which an amino acid is identical in the two compared sequences, dividing the number of identical positions by the number of compared positions and multiplying the result obtained by 100 to obtain the percentage of identity between the two sequences. The sequence comparisons between two amino acid sequences can be carried out manually or by means of computer programs known in the state of the art, such as the BLAST (Basic Local Alignment Search Tool) algorithm. As stated above, in a first aspect, the present invention refers to peptides of formula (I):

$$R_1-(X)_m-AA_1-AA_2-AA_3-AA_4-AA_5-(Y)_n-R_2 \qquad (I)$$

their cosmetically acceptable isomers, salts, solvates and/or derivatives and mixtures thereof, wherein:

X is Ala;
$AA_1$ is Leu;
$AA_2$ is His;
$AA_3$ is Lys;
$AA_4$ is Val;
$AA_5$ is Lys;
Y is Val;
n and m are selected independently of each other from 0 and 1;
$R_1$ is selected from H, substituted or unsubstituted non-cyclic aliphatic, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO— wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3 to 10 members, and substituted or unsubstituted heteroarylalkyl of 2 to 24 carbon atoms and 1 to 3 atoms other than carbon and an alkyl chain of 1 to 6 carbon atoms; and $R_2$ is selected from H, —$NR_3R_4$—, —$OR_3$ and —$SR_3$—, wherein $R_3$ and $R_4$ are independently selected from H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl.

It is contemplated that the amino acids used or present in the peptides of the present invention are L-amino acids, D-amino acids or combinations thereof. In a preferred embodiment, the amino acids used or present in the peptides of the present invention are L-amino acids.

Preferably, the isomers mentioned above are stereoisomers. It is contemplated that said stereoisomers are enantiomers or diastereoisomers. Hence, in a preferred embodiment of the present invention, the peptide is a racemic mixture, a diastereomeric mixture, a pure enantiomer or a pure diastereoisomer.

Within the scope of the present invention also included are peptides with conservative substitutions with regard to the peptides of formula (I) of the present invention. Hence, within the scope of the present invention are peptides which are substantially homologous to the peptides of formula (I) of the present invention, which have at least a 75%, preferably 80%, preferably 85%, preferably 90%, more preferably 95% and even more preferably 99% percentage of identity with a peptide of formula (I) of the present invention as disclosed herein, and which show one or more of the activities and effects disclosed herein for the peptides of the present invention, preferably all the activities and effects disclosed herein for the peptides of the present invention.

In a preferred embodiment, m is 1, and, preferably, n is 0.

In another preferred embodiment, n is 1 and, preferably, m is 0.

Preferably, $R_7$ is selected from H or $R_5$—CO—, wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_5$-$C_{O4}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3 to 10 members, and substituted or unsubstituted heteroarylalkyl of 2 to 24 carbon atoms and 1 to 3 atoms other than carbon and an alkyl chain of 1 to 6 carbon atoms. More preferably, $R_7$ is selected from H, acetyl (hereinafter, Ac), tert-butanoyl, hexanoyl, 2-methylhexanoyl, cyclohexanecarboxyl, octanoyl, decanoyl, lauroyl myristoyl, palmitoyl, stearoyl, oleoyl and linoleoyl. Even more preferably, $R_7$ is H, Ac, lauroyl, myristoyl or palmitoyl. In an even more preferred embodiment, $R_7$ is Ac or myristoyl.

Also, preferably, $R_2$ is H or $NH_2$, more preferably $NH_2$.

Therefore, in the most preferred embodiment, $R_7$ is Ac or myristoyl and $R_2$ is H or $NH_2$, more preferably $NH_2$.

In a preferred embodiment, the peptide of formula (I) is:
$R_1$-Leu-His-Lys-Val-Lys-Val-$R_2$ ($R_1$-SEQ ID NO: 2-$R_2$); or
$R_1$-Ala-Leu-His-Lys-Val-Lys-$R_2$ ($R_1$-SEQ ID NO: 3-$R_2$).

More preferably, the peptide of formula (I) is:
Myristoyl-Leu-His-Lys-Val-Lys-Val-$NH_2$ (Myristoyl-SEQ ID NO: 2-$NH_2$); or
Ac-Ala-Leu-His-Lys-Val-Lys-$NH_2$ (Ac-SEQ ID NO: 3-$NH_2$).

In the most preferred embodiment the peptide of formula (I) is:
$R_1$-Ala-Leu-His-Lys-Val-Lys-$R_2$ ($R_1$-SEQ ID NO: 3-$R_2$), even more preferably Ac-Ala-Leu-His-Lys-Val-Lys-$NH_2$ (Ac-SEQ ID NO: 3-$NH_2$).

In another most preferred embodiment the peptide of formula (I) is:
$R_1$-Leu-His-Lys-Val-Lys-Val-$R_2$ ($R_1$-SEQ ID NO: 2-$R_2$), even more preferably Myristoyl-Leu-His-Lys-Val-Lys-Val-$NH_2$ (Myristoyl-SEQ ID NO: 2-$NH_2$).

In accordance with what has already been noted above, within the scope of the present invention also included are peptides with conservative substitutions with regard to the peptides $R_1$-SEQ ID NO:2-$R_2$ or $R_1$-SEQ ID NO: 3-$R_2$. Hence, within the scope of the present invention are peptides which are substantially homologous to $R_1$-SEQ ID NO:2-$R_2$ and $R_1$-SEQ ID NO: 3-$R_2$, which have at least a 75%, preferably 80%, preferably 85%, preferably 90%, more preferably 95% and even more preferably 99% percentage of identity with $R_1$-SEQ ID NO:2-$R_2$ or $R_1$-SEQ ID NO: 3-$R_2$ and which keep one or more of the activities described herein for the peptides of the present invention, more preferably all of the activities described herein for the peptides of the present invention. $R_1$ and $R_2$ are as explained and disclosed above.

The peptides of the present invention can be produced or synthesized in accordance with any of the methods known in the state of the art, for example, by chemical synthesis, biofermentation or transgenic production. More preferably, the peptides of the present invention are produced by means of chemical synthesis.

The activities of the peptides of the present invention, this is, inhibition of elastase activity and of the production of metalloproteinases 1 and 3; and modulation of the synthesis of versican, tropoelastin, fibrillin-1 and hyaluronic acid, demonstrate, as already stated above, that said peptides (and peptides derived thereof) and compositions comprising them are suitable to be used as or in cosmetic formulations aimed at improving the viscoelastic and firming characteristics of the skin of a subject and, hence, they are useful at preventing and/or reducing the signs of skin aging (for example, wrinkles, roughness and/or sagginess).

Topical application of said peptides improves the viscoelasticity and firmness of the dermis because, as it can be directly derived from the examples included below:

There is a clear increase in the synthesis of versican, the most relevant molecule involved in this feature of the skin.

The distribution of elastic fibres is also improved as an increase in fibrillin-1 and tropoelastin, can also be observed. In addition, elastase activity is shown to be inhibited by the peptides of the present invention. As stated above, it is widely known that degradation of elastic fibres is a major contributing factor in aging, causing loss of elasticity, wrinkling, sagginess, and roughened texture of the skin. Therefore, the increase in synthesis of the key components of the elastic fibres and inhibition of their degradation provides for an improvement in the abovementioned signs of aging.

Increase in synthesis of hyaluronic acid, which improves hydration, firmness and tightness of the skin.

Decrease in the production of metalloproteinases 1 and 3 (downregulation of their expression), this is, a decrease in the production of molecules responsible for the degradation of the ECM.

In addition, as can be directly derived from the examples included below, the peptides of the present invention (and peptides derived thereof) and compositions comprising them provide for an improved quality of the firmness of the skin (for example, by improving the recovery of the skin to external stimuli or aggressions), preferably of the face skin.

Therefore, the peptides of the present invention solve the above-mentioned technical problem present in the state of the art.

In a second aspect, the present invention refers to a composition comprising a peptide of the present invention, as disclosed herein.

In a preferred embodiment of the present invention, the composition is a cosmetic composition which provides for the prevention and/or reduction of signs of skin aging, including chronological and/or environmental aging. In addition, the cosmetic composition of the present invention improves viscoelasticity and firmness of the skin due to the above-mentioned features of the peptides of the present invention.

It is contemplated that the cosmetic composition of the present invention comprises one peptide of the present invention or a combination or mixture of the peptides of the present invention.

In an embodiment, the cosmetic composition disclosed above comprises 0.1%-0.0001% (mass/volume; this is, mg/ml) of a peptide of the present invention or a combination of peptides of the present invention. More preferably, said composition comprises 0.05%-0.001% (m/v) of a peptide of the present invention or a combination of peptides of the present invention.

It is contemplated that the cosmetic composition of the present invention also comprises additional cosmetic ingredients. Said additional cosmetic ingredients comprise those usually used in the state of the art as, for example, adjuvants such as stabilizer, solubilizer, vitamin, colorant and perfumery; carriers; and/or other cosmetic active ingredients.

Said additional cosmetic ingredients, must be physically and chemically compatible with the rest of the components of the composition and, especially, with the peptides of the present invention comprised in the composition of the present invention. Likewise, the nature of said additional cosmetic ingredients must not unacceptably alter the benefits of the compounds of the present invention. Said additional cosmetic ingredients may be of a synthetic or natural origin, such as, for example, plant extracts, or they can be derived from a biofermentation process (see, for example, CTFA Cosmetic Ingredient Handbook, Eleventh Edition (2006)).

It is contemplated that the additional cosmetic ingredients mentioned above comprise those ingredients commonly used in compositions for caring for and/or cleaning skin and/or hair such as, for example, agents inhibiting melanin synthesis, whitening or depigmenting agents, anti-aging agents, agents inhibiting NO-synthase, antioxidants, anti-atmospheric pollution and/or free radical trapping agents, anti-glycation agents, emulsifying agents, emollients, organic solvents, liquid propellants, skin conditioners such as for example wetting agents, moisture retaining substances, alpha hydroxy acids, moisturizers, vitamins, pigments or colorants, dyes, gelling polymers, thickeners, surfactants, softeners, other anti-wrinkle agents, agents capable of reducing or eliminating bags under the eyes, exfoliating agents, antimicrobial agents, antifungal agents, bactericides, agents stimulating dermal or epidermal macromolecule synthesis and/or capable of preventing or inhibiting their degradation, such as for example agents stimulating collagens synthesis, agents stimulating elastin synthesis, agents stimulating laminin synthesis, agents inhibiting collagen degradation, agents inhibiting elastin degradation, agents stimulating fibroblast proliferation, agents stimulating keratinocyte proliferation, agents stimulating keratinocyte differentiation, agents stimulating lipid synthesis and synthesis of components of the stratum corneum (ceramides, fatty acids, etc.), dermorelaxing agents, agents stimulating glycosaminoglycan synthesis, DNA repairing agents, DNA protecting agents, agents stimulating proteasome activity, anti-pruritus agents, agents for treating sensitive skin, reaffirming agents, astringent agents, sebum production regulating agents, agents stimulating lipolysis, anti-cellulite agents, calming agents, anti-inflammatory agents, agents acting on capillary circulation and/or microcirculation, agents acting on cell mitochondria, agents intended to improve the derma-epidermal junction, preservatives, perfumes, chelating agents, plant extracts, essential oils, marine extracts, agents derived from a biofermentation process, mineral salts, cell extracts and/or solar filters (organic or mineral photoprotective agents active against ultraviolet A and B rays) among others.

In an embodiment, at least one of the additional cosmetic ingredients is a cosmetic active principle or substance which may exert the same, similar, complementary or different cosmetic activities as those disclosed above for the peptides of the present invention.

In a preferred embodiment, the cosmetic composition of the present invention comprises other anti-aging agents, for example, agents stimulating the expression and/or synthesis of collagen I, III, IV and/or VI and laminin; agents stimulating the synthesis of glycosaminoglycans or hyaluronic acid; agents stimulating the expression and/or synthesis of elastin and other elastic fibers-related proteins; agents inhibiting collagen and/or elastic fibers degradation; agents stimulating the expression and/or synthesis of mitochondria-related proteins (for example, sirtuins and aconitase); agents stimulating the expression and/or synthesis of focal adhesion proteins; agents stimulating keratinocytes and/or fibroblasts proliferation and/or differentiation; antioxidants; anti-atmospheric pollution and/or free radical trapping agents; anti-glycation agents; detoxifying agents; agents decreasing chronological; environmental aging and inflammaging; and agents decreasing melanin production and/or inhibiting tyrosinase and/or agents stimulating lipid synthesis and synthesis of components of the epidermis (keratins) and more specifically the stratum corneum (keratins, ceramides, filaggrin, loricrin and SPRR1B).

In addition, the cosmetic composition of the present invention can be formulated as any form usually used in the state of the art as, for example, solution, suspension, emulsion, paste, gel, cream, powder, spray, lotion, oil, liniment, serum, mousse, ointment, bar or pencil including "leave on" and "rinse-off" formulations. The cosmetic composition of the present invention can also be incorporated by means of techniques known in the state of the art to different types of solid accessories such as towelettes, hydrogels, adhesive (or non-adhesive) patches or face masks, or it could be incorporated to different make-up line products such as concealers, make-up foundations, lotions or make-up removal lotions, among others.

It is also contemplated that the cosmetic composition of the present invention or the peptide of the present invention, both as disclosed herein, can also be incorporated in cosmetic sustained release systems and/or carriers such as liposomes, milliparticles, microparticles and nanoparticles, as well as in sponges, vesicles, micelles, millispheres, microspheres, nanospheres, liposheres, millicapsules, microcapsules and nanocapsules, as well as in microemulsions and nanoemulsions, for the purpose of obtaining greater penetration of the active ingredient.

In a preferred embodiment, the cosmetic composition of the present invention is suited or adapted to be applied topically, in the face and/or the body of a subject, more preferably in the face, neck and/or double chin of a human.

In a third aspect, the present invention relates to the use as a cosmetic of the peptides or the cosmetic compositions of the present invention to prevent and/or reduce the signs of skin aging and/or for skin firming in a subject.

The peptide, alone or within the composition of the present invention, is used in a cosmetically effective amount. More preferably, said cosmetically effective amount is of 0.1%-0.0001% (m/v), even more preferably, said cosmetically effective amount is of 0.05%-0.001% (m/v).

In an embodiment, skin aging is chronological and/or environmental aging.

In a preferred embodiment, the signs of skin aging are wrinkles, roughness and/or sagginess.

Hence, in a preferred embodiment, the above-mentioned use as a cosmetic of the peptides or cosmetic compositions of the present invention is to prevent and/or reduce signs of skin aging (including chronological and/or environmental aging), more preferably wrinkles, roughness and sagginess.

In another preferred embodiment, the use as a cosmetic of the peptides or cosmetic compositions of the present invention is for skin firming, more preferably for improving the quality of the firmness of the skin (preferably, facial skin), even more preferably, for improving the recovery of the skin to external stimuli or aggressions.

The use as a cosmetic of the peptides or cosmetic compositions of the present invention, as already stated above, also improve the viscoelasticity of the skin.

Also in a preferred embodiment, the subject is a human.

It is contemplated that in the use as a cosmetic of the present invention as disclosed above, the peptide or the composition of the present invention is used in combination with one or more additional active principles and/or compositions. Said one or more active principles and/or compositions may be used before, together or after the peptide or composition of the present invention.

In a preferred embodiment, in the use of the present invention as disclosed above, the peptide and/or the cosmetic composition of the present invention is applied topically, in the face and/or body of the subject, more preferably in the face, neck and/or double chin of a human.

In a fourth aspect, the present invention refers to the cosmetic use of the peptides or the cosmetic compositions of the present invention, as described above, to prevent, and/or reduce the signs of skin aging and/or for skin firming in a subject.

The peptide, alone or within the composition of the present invention, is used in a cosmetically effective amount. More preferably, said cosmetically effective amount is of 0.1%-0.0001% (m/v), even more preferably, said cosmetically effective amount is of 0.05%-0.001% (m/v).

In an embodiment, skin aging is chronological and/or environmental aging.

In a preferred embodiment, the signs of skin aging (chronological and/or environmental aging) are wrinkles, roughness and/or sagginess.

Hence, in a preferred embodiment, the cosmetic use of the peptides or compositions of the present invention is to prevent and/or reduce signs of skin aging (including, as stated above, chronological and/or environmental aging), more preferably said signs are wrinkles, roughness and/or sagginess.

In another preferred embodiment, the cosmetic use of the peptides or compositions of the present invention is for skin firming, more preferably for improving the quality of the firmness of the skin (preferably, facial skin), even more preferably, for improving the recovery of the skin to external stimuli or aggressions.

The cosmetic use of the peptides or cosmetic compositions of the present invention, as already stated above, also improve the viscoelasticity of the skin.

Also in a preferred embodiment, the subject is a human.

It is contemplated that in the cosmetic use of the present invention as disclosed above, the peptide or the composition of the present invention is used in combination with one or more additional active principles and/or compositions. Said one or more active principles and/or compositions may be used before, together or after the peptide or composition of the present invention.

In a preferred embodiment, in the cosmetic use of the present invention as disclosed above, the peptide and/or the cosmetic composition of the present invention is applied topically, in the face and/or body of the subject, more preferably in the face, neck and/or double chin of a human.

In a fifth aspect, the present invention refers to a method to prevent and/or reduce the signs of skin aging in a subject in need thereof, characterized in that it comprises the use of a peptide or a cosmetic composition of the present invention.

The peptide, alone or within the composition of the present invention, is used in a cosmetically effective amount. More preferably, said cosmetically effective amount is of 0.1%-0.0001% (m/v), even more preferably, said cosmetically effective amount is of 0.05%-0.001% (m/v).

In an embodiment, skin aging is chronological and/or environmental aging.

In a preferred embodiment, the signs of skin aging (chronological and/or environmental aging) are wrinkles, roughness and/or sagginess.

In a preferred embodiment, the subject is a human.

It is contemplated that the peptide or composition of the present invention is used in the method of the present invention by direct application to the zone of the skin of the human body. In a preferred embodiment, the peptide or composition of the present invention is applied in the form of solution, suspension, emulsion, paste, gel, cream, powder, spray, lotion, oil, liniment, serum, mousse, ointment, bar or pencil including "leave on" and "rinse-off" formulations. As stated above, it is also contemplated that the peptide or composition of the present invention can also be incorporated by means of techniques known in the state of the art to different types of solid accessories such as towelettes, hydrogels, adhesive (or non-adhesive) patches or face masks, or it can be incorporated to different make-up line products such as concealers, make-up foundations, lotions or make-up removal lotions, among others; and, hence used in any of said forms in the method of the present invention.

As stated above, the method disclosed above is a cosmetic method with cosmetic effect.

It is contemplated that in the method of the present invention as disclosed above, the peptide or the composition of the present invention is used in combination with one or more additional active principles and/or compositions. Said one or more active principles and/or compositions may be used before, together or after the peptide or composition of the present invention.

In a preferred embodiment, in the method of the present invention as disclosed above, the peptide and/or the cosmetic composition of the present invention is applied topically, in the face and/or body of the subject, more preferably in the face, neck and/or double chin of a human.

In a final aspect, the present invention refers to a method for skin firming in a subject in need thereof, characterized in that it comprises the use of a peptide or a composition of the present invention.

The method for skin firming of the present invention includes both, prevention of the loss of firmness (and viscoelasticity) of the skin, as well as treatment or correction of the loss of firmness (and viscoelasticity) of the skin.

In a preferred embodiment, the method of the present invention is for improving the quality of the firmness of the skin (preferably, facial skin), even more preferably, for improving the recovery of the skin to external stimuli or aggressions.

The peptide, alone or within the composition of the present invention, is used in a cosmetically effective amount. More preferably, said cosmetically effective amount is of 0.1%-0.0001% (m/v), even more preferably, said cosmetically effective amount is of 0.05%-0.001% (m/v).

In an embodiment, skin aging is chronological and/or environmental aging.

In a preferred embodiment, the subject is a human.

It is contemplated that the peptide or composition of the present invention is used in the method of the present invention by direct application to the zone of the skin of the human body. In a preferred embodiment, the peptide or composition of the present invention is applied in the form of solution, suspension, emulsion, paste, gel, cream, powder, spray, lotion, oil, liniment, serum, mousse, ointment, bar or pencil including "leave on" and "rinse-off" formulations. As stated above, it is also contemplated that the peptide or composition of the present invention can also be incorporated by means of techniques known in the state of the art to different types of solid accessories such as towelettes, hydrogels, adhesive (or non-adhesive) patches or face masks, or it can be incorporated to different make-up line products such as concealers, make-up foundations, lotions or make-up removal lotions, among others; and, hence used in any of said forms in the method of the present invention.

As stated above, the method disclosed above is a cosmetic method with cosmetic effect.

It is contemplated that in the method of the present invention as disclosed above, the peptide or the composition of the present invention is used in combination with one or more additional active principles and/or compositions. Said one or more active principles and/or compositions may be used before, together or after the peptide or composition of the present invention.

In a preferred embodiment, in the method of the present invention as disclosed above, the peptide and/or the cosmetic composition of the present invention is applied topically, in the face and/or body of the subject, more preferably in the face, neck and/or double chin of a human.

As already noted above, the peptides of the present invention (and, hence, also the cosmetic compositions of the present invention) have shown a wide spectrum of activities related with the maintenance and production of the ECM. Therefore, said peptides are suited to be used in cosmetics for skin firming and/or prevention, reductions and/or removal of signs of skin aging.

BRIEF DESCRIPTION OF DRAWINGS

To allow a better understanding, the present invention is described in more detail below with reference to the enclosed drawings, which are presented by way of example, and with reference to illustrative and non-limitative examples.

FIG. 1 (A) shows the result of percentage of elastase inhibition obtained for the treatment with peptide Myristoyl-SEQ ID NO: 2-$NH_2$ in the three concentrations tested. Columns from left to right in the x-axis: positive control of inhibition (Phenylmethanesulfonyl (PMSF)), 0.001 mg/ml, 0.005 mg/ml and 0.01 mg/ml of the peptide of the present invention. On its side, FIG. 1 (B) shows the result of percentage of elastase inhibition obtained for the treatment with peptide Ac-SEQ ID NO: 3-$NH_2$ in the three concentrations tested. Columns from left to right in the x-axis: positive control of inhibition (PMSF), 0.005 mg/ml, 0.01 mg/ml and 0.05 mg/ml of the peptide of the present invention. For both, FIGS. 1 (A) and 1 (B), they axis shows the percentage of elastase activity inhibition (with regard to the positive control sample).

(MMP1), Metalloproteinase-3 (MMP3), Fibronectin 1 (FN1), Fibrillin-1 (FBN1) and Versican (VCAN) genes, and x axis refers to fold change vs basal control. Negative fold change means that the corresponding gene is downregulated; and a positive fold change means that the corresponding gene is upregulated.

Figure 7:
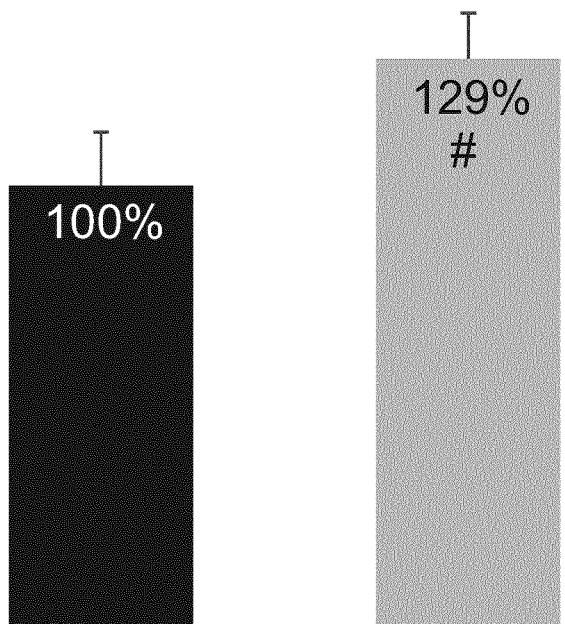

FIG. 7 shows the modulation of versican synthesis by 0.005 mg/ml of Ac-SEQ ID NO: 3-$NH_2$ after its topical application in a cosmetic formulation at 1% (m/v) from a stock solution at 0.05% (m/v) on human skin explants. This is shown by means of the quantity of skin surface (epidermis and dermis) occupied by versican protein in comparison with the quantity of skin surface occupied by versican in the basal control (non-treated skin explants), wherein the quantity of skin surface occupied by versican in the basal control is set to 100% and then the comparison with the skin explant treated with Ac-SEQ ID NO: 3-N $H_2$ is performed. Columns from left to right in the x-axis refer to: non-treated skin explants and skin explant sample treated with 0.005 mg/ml of Ac-SEQ ID NO: 3-$NH_2$, respectively. The y-axis shows the percentage of skin surface occupied by versican protein with regard to the basal control.

Figure 8:
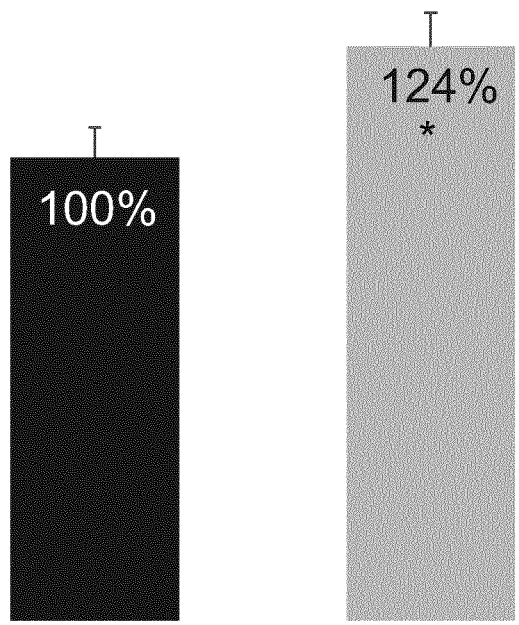

FIG. 8 shows the modulation of fibrillin-1 synthesis by 0.005 mg/ml of Ac-SEQ ID NO: 3-$NH_2$ after its topical application in a cosmetic formulation at 1% (m/v) from a stock solution at 0.05% (m/v) on human skin explants. This is shown by means of the quantity of skin surface (epidermis and dermis) occupied by fibrillin-1 protein in comparison with the quantity of skin surface occupied by fibrillin-1 in the basal control (non-treated skin explants), wherein the quantity of skin surface occupied by fibrillin-1 in the basal control is set to 100% and then the comparison with the skin explant treated with Ac-SEQ ID NO: 3-N $H_2$ is performed. Columns from left to right in the x-axis refer to: non-treated skin explants and skin explant sample treated with 0.005 mg/ml of Ac-SEQ ID NO: 3-N $H_2$, respectively. The y-axis shows the percentage of skin surface occupied by fibrillin-1 protein with regard to the basal control.

Figure 9B:
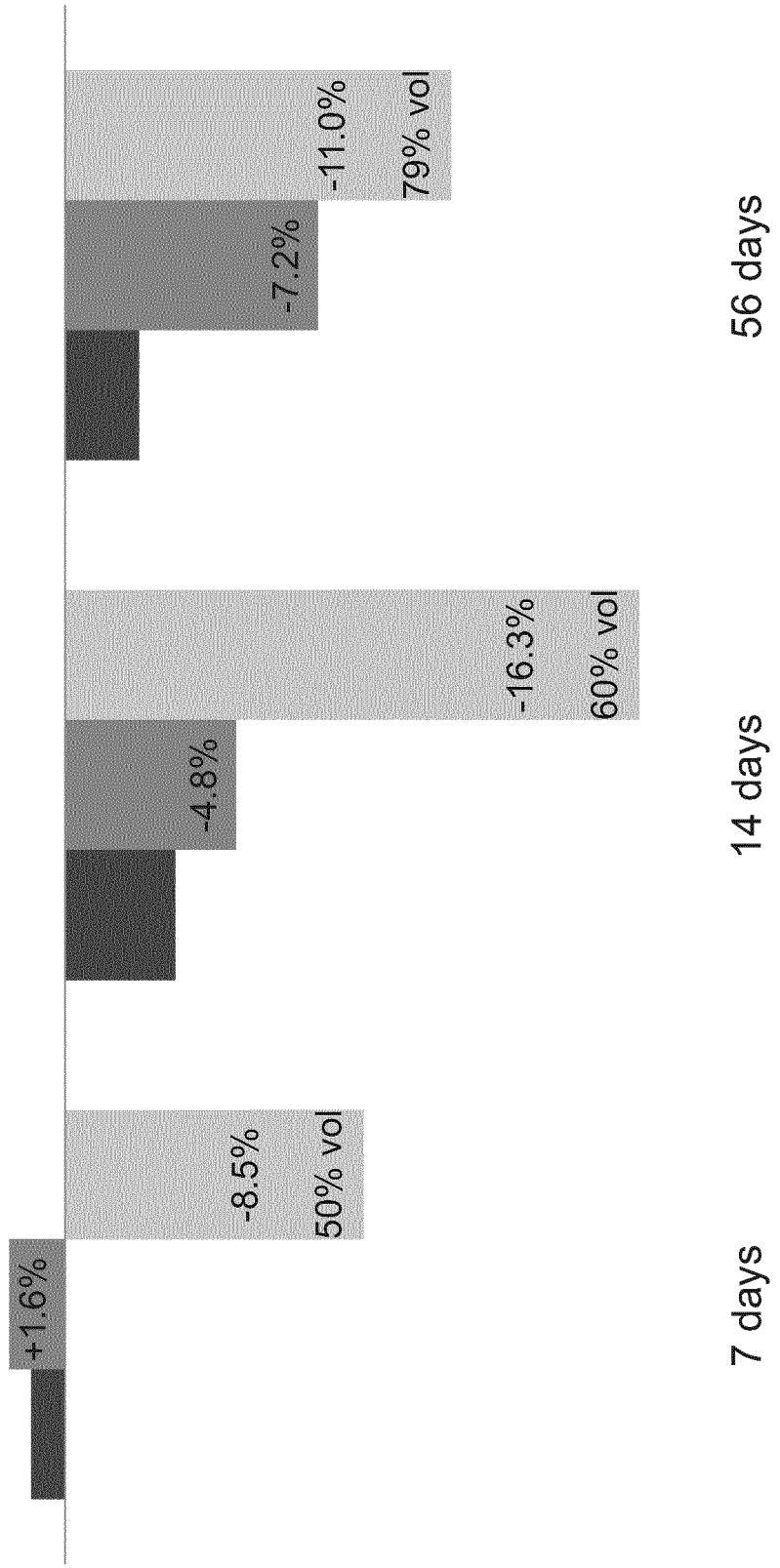
Figure 9C:
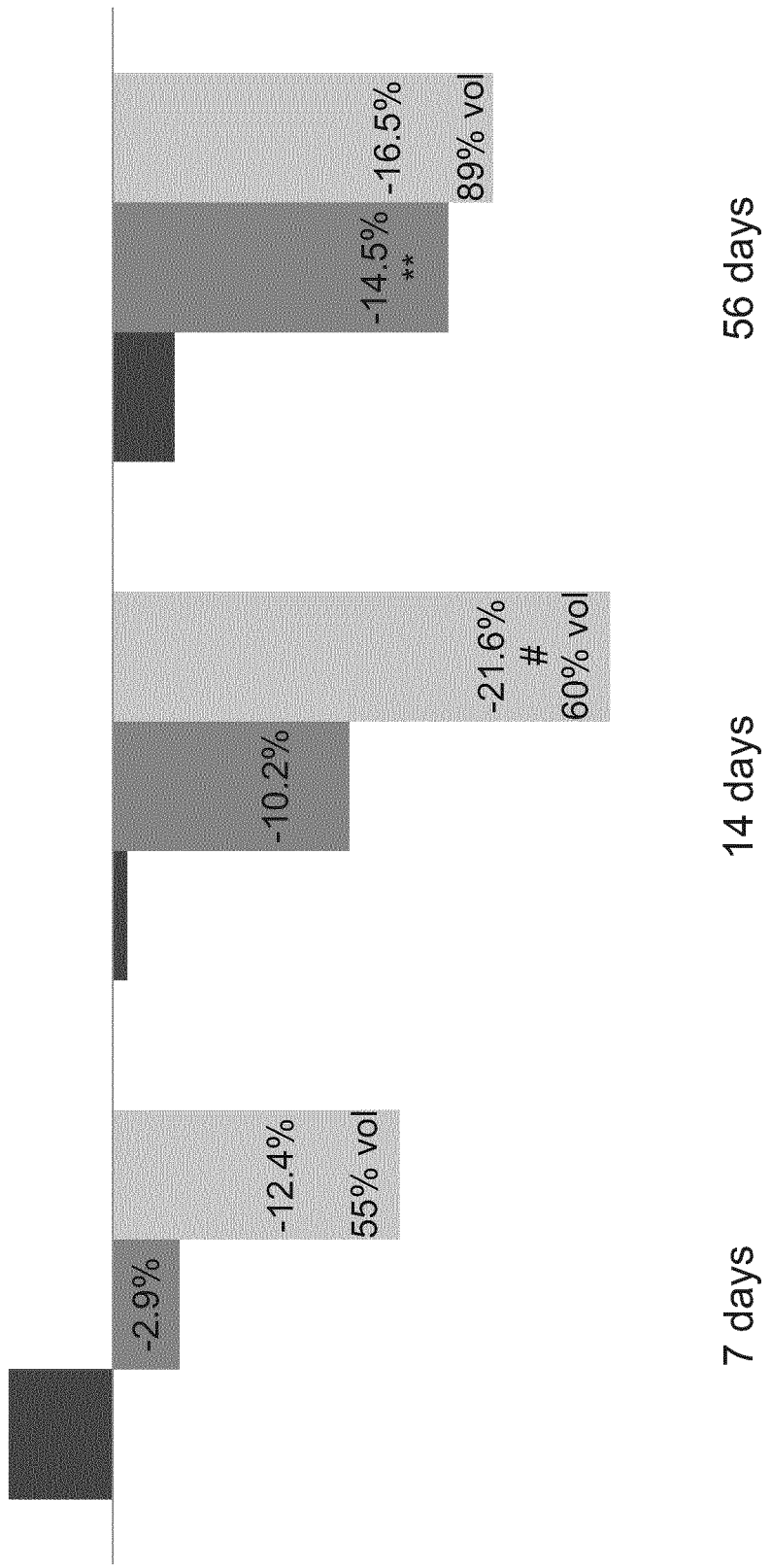

FIG. 9 shows the efficacy of Ac-SEQ ID NO: 3-$NH_2$ after its topical application on female Caucasian volunteers. A cosmetic formulation comprising 3% (m/v) of Ac-SEQ ID NO: 3-N $H_2$ peptide from a stock at 0.05% (m/v) or a placebo were applied each on one half of the face (cheek) and on each volunteer. FIG. 9 (A) shows the cheek deformation of the volunteers by Dynaskin (Dynaskin is an add-on on the dermaTop System to provide firmness evaluation with a complete non-contact method; it produces a deformation close to the clinical approach by blowing air perpendicular to the area of interest or with a dedicated angle of 45°; the System can measure in any position; the 3D sensor, using fringe projection techniques, captures just before deformation, the shape of the local surface, then when the deformation is applied and just after it) as measured by means of the average percentage of volume ($mm^3$) change of the cheek with regard to the volume of the cheek at the beginning of the treatment (time=0 days). In the x-axis, from left to right the groups of three columns each corresponds to: day 7, day 14 and day 56 all from the beginning of the treatment, respectively. Also in the x-axis, in each of the three groups of columns, the columns, from left to right correspond to: volunteers treated with a cosmetic formulation (placebo), with the same formulation but also comprising 0.015 mg/ml of Ac-SEQ ID NO: 3-$NH_2$ and responsive volunteers only (from those treated with the cosmetic formulation comprising 0.015 mg/ml of Ac-SEQ ID NO: 3-$NH_2$). The y axis shows the percentage of volume variations versus initial time for average of the corresponding treatment group or responsive volunteers. FIG. 9 (B) shows the cheek deformation of the volunteers as measured by means of percentage of variations in area ($mm^2$) of the cheek region deformed by Dynaskin with regard to the area at the beginning of the treatment (time=0 days). In the x-axis, from left to right the groups of three columns each corresponds to: day 7, day 14 and day 56 all from the beginning of the treatment, respectively. Also in the x-axis, in each of the three groups of columns, the columns, from left to right correspond to: volunteers treated with a cosmetic formulation (placebo), with the same formulation but also containing 0.015 mg/ml of Ac-SEQ ID NO: 3-$NH_2$ and responsive volunteers only (from those treated with the cosmetic formulation comprising 0.015 mg/ml of Ac-SEQ ID NO: 3-$NH_2$). The y-axis shows the percentage of area variations versus initial time for average of the corresponding treatment group or responsive volunteers. On its side, FIG. 9 (C) shows the cheek deformation of the volunteers as measured by means of percentage of variations in depth (mm) of the cheek region deformed by Dynaskin with regard to the area at the beginning of the treatment (time=0 days). In the x-axis, from left to right the groups of three columns each corresponds to: day 7, day 14 and day 56 all from the beginning of the treatment, respectively. Also in the x-axis, in each of the three groups of columns, the columns, from left to right correspond to: volunteers treated with a cosmetic formulation (placebo), with the same formulation but also comprising 0.015 mg/ml of Ac-SEQ ID NO: 3-$NH_2$ and responsive volunteers only (from those treated with the cosmetic formulation comprising 0.015 mg/ml of Ac-SEQ ID NO: 3-$NH_2$). The y-axis shows the percentage of depth variations versus initial time for average of the corresponding treatment group or responsive volunteers. In FIGS. 9(A) to 9(C), the percentage noted with the indication "vol" refers to the percentage of responsive volunteers regarding the total number of volunteers treated with the cosmetic formulation comprising the peptide of the present invention.

EXAMPLES

Abbreviations

The abbreviations used for amino acids follow the 1983 IUPAC-IUB Joint Commission on Biochemical Nomenclature recommendations outlined in Eur. J. Biochem. (1984) 138:937.

2-ClTrt, 2-chlorotrityl; Ac, acetyl; Ala, alanine; Arg, arginine; Boc, tert-butyloxycarbonyl; C-terminal, carboxy-terminal; DCM, dichloromethane; DIEA, N,N'-diisopropylethylamine; DIPCDI, N,N'-diisopropylcarbodiimide; DMF, N,N-dimethylformamide; equiv, equivalent; ESI-MS, electrospray ionization mass spectrometry; Fmoc, 9-fluorenylmethyloxycarbonyl; His, histidine; HOBt, 1-hydroxybenzotriazole; HPLC, high performance liquid chromatography; HDFa, human dermal fibroblasts; Ile, Isoleucine; INCI, International Nomenclature of Cosmetic Ingredients; MBHA, p-methylbenzhydrylamine; Leu, leucine; Lys, lysine; Me, methyl; MeCN, acetonitrile; MeOH, methanol; Myr, myristoyl; N-terminal, amino-terminal; Palm, palmitoyl; Pbf, 2,2,4,6,7-pentamethyldihydrobenzofuran-5-sulfonyl; PMSF, Phenylmethanesulfonyl; RT, room temperature; TFA, trifluoroacetic acid; TIS, triisopropylsilane; Trp, tryptophan; Trt, triphenylmethyl or trityl; Val, valine; Z, benzyloxycarbonyl.

Regarding the chemical synthesis procedures included in the examples, it is noted that all synthetic processes were carried out in polypropylene syringes fitted with porous polyethylene discs or Pyrex® reactors fitted with porous plates. All the reagents and solvents were synthesis quality and were used without any additional treatment. The solvents and soluble reagents were removed by suction. The Fmoc group was removed with piperidine-DMF (2:8, v/v) (at least 1×1 min, 2×10 min, 5 mL/g resin) (Lloyd Williams P. et al., *Chemical Approaches to the Synthesis of Peptides and Proteins*, C R C, 1997, Boca Raton (Fla., USA)). Washes between stages of deprotection, coupling, and, again, deprotection, were carried out with DMF (3×1 min) and DCM (3×1 min) each time using 10 ml solvent/g resin. Coupling reactions were performed with 3 ml solvent/g resin. The control of the couplings was performed by carrying out the ninhydrin test (Kaiser E. et al., Anal. Biochem., 1970, 34: 595598). All synthetic reactions and washes were carried out at RT.

Example 1. Synthesis and Preparation of the Peptides of the Present Invention

Obtaining Fmoc-$(X)_m$-$AA_1$-$AA_2$-$AA_3$-$AA_4$-$AA_5$-$(Y)_n$—$R_2$-Rink-MBHA-resin, wherein $AA_1$ is L-Leu; $AA_2$ is His; $AA_3$ is L-Lys; $AA_4$ is L-Val; $AA_5$ is L-Lys; Y is L-Val; n is 1; and m is 0.

Weights were normalized. 4.8 g (2.5 mmol) of the Fmoc-Rink-MBHA resin with a functionalization of 0.52 mmol/g were treated with piperidine-DMF according to the described general protocol in order to remove the Fmoc group. 2.55 g of Fmoc-L-Val-OH (7.5 mmol; 3 equiv) were incorporated onto the deprotected resin in the presence of DIPCDI (1.17 mL; 7.5 mmol; 3 equiv) and HOBt (1.01 g; 7.5 mmol; 3 equiv) using DMF as a solvent for one hour.

The resin was then washed as described in the general methods and the deprotection treatment of the Fmoc group was repeated to couple the next amino acid. Following the previously described protocols 3.51 g of Fmoc-L-Lys(Boc)-OH (7.5 mmol; 3 equiv); subsequently 2.55 g of Fmoc-L-Val-OH (7.5 mmol; 3 equiv); subsequently 3.51 g of Fmoc-L-Lys(Boc)-OH (7.5 mmol; 3 equiv); subsequently 4.65 g Fmoc-L-His(Trt)-OH (7.5 mmol; 3 equiv) and subsequently 2.65 g Fmoc-L-Leu-OH (7.5 mmol; 3 equiv) were coupled, sequentially, each coupling in the presence of 1.01 g of HOBt (7.5 mmol; 3 equiv) and 1.17 mL of DIPCDI (7.5 mmol; 3 equiv). As already noted above, between each amino acid addition step, a deprotection treatment of the Fmoc group was performed.

After the synthesis, the peptide resins were washed with DCM (5 times for 3 minutes each one) and dried under vacuum.

Obtaining Fmoc-$(X)_m$-$AA_1$-$AA_2$-$AA_3$-$AA_4$-$AA_5$-$(Y)_n$—$R_2$-Rink-MBNA, wherein X is L-Ala; $AA_1$ is L-Leu; $AA_2$ is His; $AA_3$ is L-Lys; $AA_4$ is L-Val; $AA_5$ is L-Lys; m is 1; and n is 0.

Weights were normalized. 4.8 g (2.5 mmol) of the Fmoc-Rink-MBHA resin with a functionalization of 0.52 mmol/g were treated with piperidine-DMF according to the described general protocol in order to remove the Fmoc group. 3.51 g of Fmoc-L-Lys(Boc)-OH (7.5 mmol; 3 equiv) were incorporated onto the deprotected resin in the presence of DIPCDI (1.17 mL; 7.5 mmol; 3 equiv) and HOBt (1.01 g; 7.5 mmol; 3 equiv) using DMF as a solvent for one hour.

The resin was then washed as described in the general methods and the deprotection treatment of the Fmoc group was repeated to couple the next amino acid. Following the previously described protocols 2.55 g of Fmoc-L-Val-OH (7.5 mmol; 3 equiv); subsequently 3.51 g of Fmoc-L-Lys(Boc)-OH (7.5 mmol; 3 equiv); subsequently 4.65 g Fmoc-L-His(Trt)-OH (7.5 mmol; 3 equiv); subsequently 2.65 g Fmoc-L-Leu-OH (7.5 mmol; 3 equiv) and subsequently 2.33 g Fmoc-L-Ala-OH (7.5 mmol; 3 equiv) were coupled, sequentially, each coupling in the presence of 1.01 g of HOBt (7.5 mmol; 3 equiv) and 1.17 mL of DIPCDI (7.5 mmol; 3 equiv). As already noted above, between each amino acid addition step, a deprotection treatment of the Fmoc group was performed.

After the synthesis, the peptide resins were washed with DCM (5 times for 3 minutes each one) and dried under vacuum.

Using the synthesis procedures mentioned above, with the required selection of amino acids, the following sequences were synthesized:
Leu-His-Lys-Val-Lys-Val (SEQ ID NO: 2); and
Ala-Leu-His-Lys-Val-Lys (SEQ ID NO: 3).

Example 2. Removal of Fmoc N-Terminal Protective Group of the Peptides Synthesized in Accordance with Example 1

The N-terminal Fmoc group of the peptidyl resins was deprotected with 20% piperidine in DMF (1×1 min+2×10 min) (Lloyd Williams P. et al. (1997) "*Chemical Approaches to the Synthesis of Peptides and Proteins*" CRC, Boca Raton (Fla., USA)). The peptidyl resins were washed with DMF (5×1 min), DCM (4×1 min), and dried under vacuum.

Example 3. Process for Introducing the $R_1$ Acetyl Group onto the Peptidyl Resins Obtained in Accordance with Example 2

1 mmol (1 equiv) of the peptidyl resins obtained in accordance with Example 2 was treated with 25 equivalents of acetic anhydride in the presence of 25 equivalents of DIEA using 5 mL of DMF as a solvent. They were left to react for 30 minutes, after which the peptidyl resins were washed with DMF (5×1 min), DCM (4×1 min), and were dried under vacuum.

Example 4. Process for Introducing the $R_1$ Myristoyl Group onto the Peptidyl Resins Obtained in Example 2

10 equivalents of pre-dissolved myristic acid in DMF (1 mL) were incorporated onto 1 mmol (1 equiv) of the peptidyl resins obtained in Example 2, in the presence of 10 equivalents of HOBt and 10 equivalents of DIPCDI. They were allowed to react overnight (approximately 15 hours), after which the resins were washed with DMF (5×1 min), DCM (4×1 min), MeOH (5×1 min) and were dried under vacuum.

Example 5. Cleavage Process from the Polymeric Support of the Peptidyl Resins Obtained in Accordance with Example 2, 3 and 4

Weights were normalized. 200 mg of the dried peptidyl resin obtained in any of Examples 2, 3 or 4 were treated with 5 mL of TFA/TIS/$H_2O$ (90:5:5) for 2 hours at room temperature under stirring. The filtrates were collected and precipitated using 50 mL (8 to 10-fold) of cold diethyl ether. The ethereal solutions were evaporated to dryness at reduced pressure and room temperature, the precipitates were redissolved in 50% MeCN in $H_2O$ and lyophilized.

Example 6. Characterization of the Peptides Synthesized and Prepared in Accordance with Example 5

HPLC analysis of the peptides obtained in accordance with example 5 was carried out with a Shimadzu equipment (Kyoto, Japan) using a reverse-phase column (150×4.6 mm, XBridge Peptide BEH $C_{18}$, 3.5 µm, Waters, USA) in gradients of MeCN (+0.036% TFA) in $H_2O$ (+0.045% TFA) at a flow rate of 1.25 mL/min and detection was carried out at 220 nm. All peptides showed a purity exceeding 80%. The identity of the peptides obtained was confirmed by ESI-MS in a Water ZQ 4000 detector using MeOH as the mobile phase and a flow rate of 0.2 mL/min. Results obtained demonstrated that the peptides Myristoyl-Leu-His-Lys-Val-Lys-Val-N $H_2$ (Myristoyl-SEQ ID NO: 2-$NH_2$); and Ac-Ala-Leu-His-Lys-Val-Lys-$NH_2$ (Ac-SEQ ID NO: 3-$NH_2$) were effectively synthesized.

Example 7. Measurement of Elastase Activity Inhibition

Both peptides Myristoyl-SEQ ID NO: 2-$NH_2$ and Ac-SEQ ID NO: 3-$NH_2$, synthesized in accordance with examples 1 to 5, were tested for their ability to inhibit elastase activity.

Peptide Ac-SEQ ID NO: 3-$NH_2$ was diluted in $H_2O$ to a concentration of 0.005 mg/ml, 0.01 mg/ml and 0.05 mg/ml and peptide Myristoyl-SEQ ID NO: 2-$NH_2$ was diluted to a concentration of 0.001 mg/ml, 0.005 mg/ml and 0.01 mg/ml. Peptide dilutions were then incubated with elastase enzyme in controlled conditions. TRIS buffer and Phenylmethane-sulfonyl (hereinafter, PMSF) were used as negative and positive controls for the inhibition of elastase activity, respectively. The subsequent addition of the specific enzyme substrate started the enzymatic reaction, which was monitored by means of absorbance at 405 nm using a plate reader. Absorbance correlated with enzymatic activity and, hence, the elastase inhibitory activity could be easily obtained.

Figure 1A:
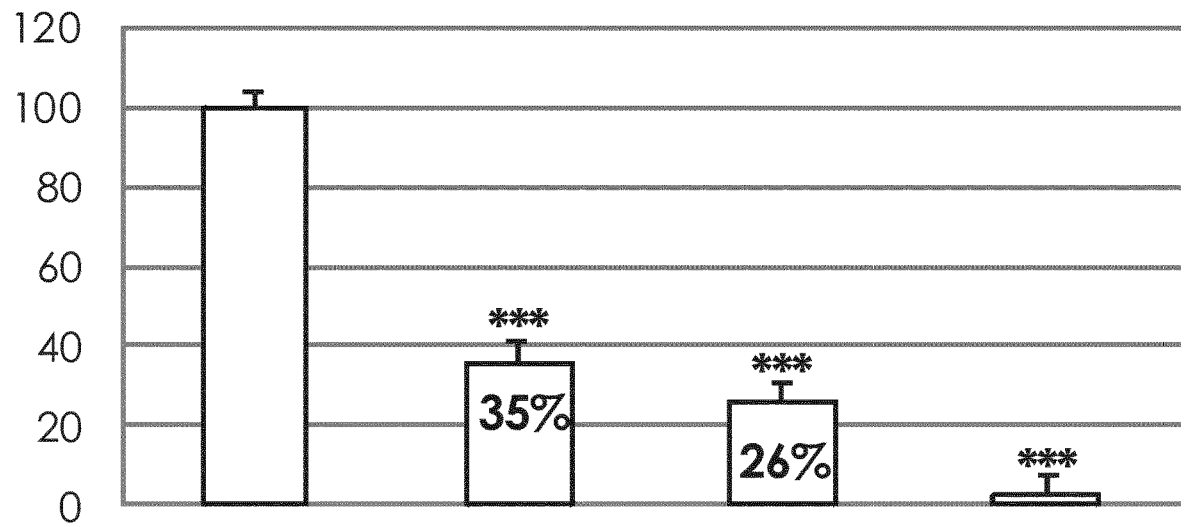
FIG. 1 shows the percentage of elastase inhibition (and, hence, the protective role against extracellular matrix degradation) of the peptides of the present invention in comparison with the positive control (this is, stablishing the percentage of elastase inhibition of the positive control sample as 100% and then performing the comparison with the rest of the samples).
Figure 1B:
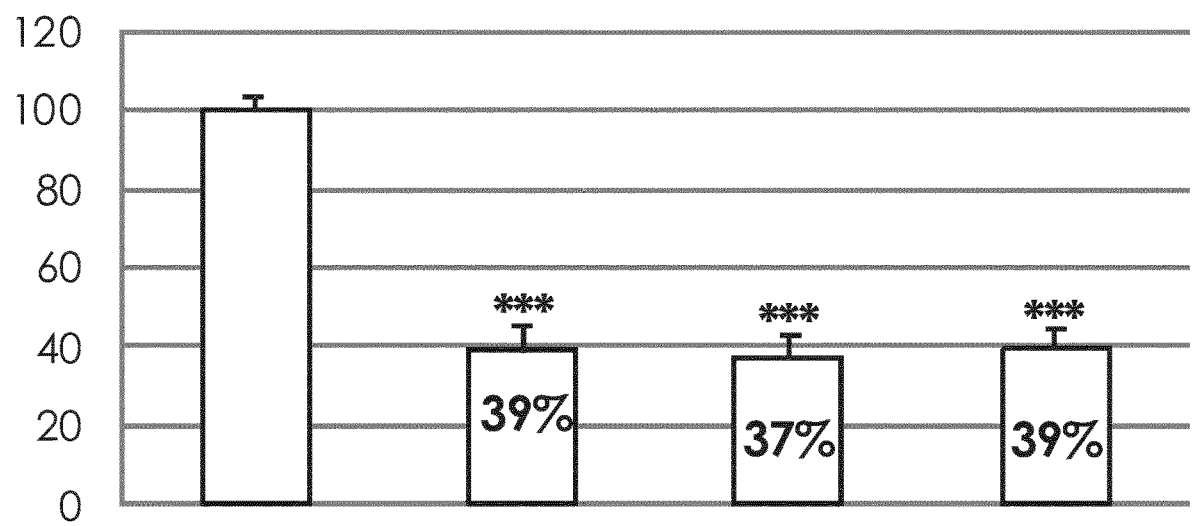

The results obtained in this example appear summarized in FIG. 1. In said figure, it can be seen that all concentrations tested of Ac-SEQ ID NO: 3-$NH_2$ showed a significant elastase inhibitory activity which was of around 39% of that seen in the positive control sample. On its side, the peptide Myristoyl-SEQ ID NO:2-$NH_2$, in the two lower concentrations tested also showed activity inhibiting elastase, which was between 35% and 26% of that seen in the positive control sample. No inhibition of elastase activity was observed in the negative control, this is, samples treated or incubated with TRIS buffer (not shown in FIG. 1).

Therefore, it can be concluded that said peptides were able to inhibit elastase under the conditions tested.

Example 8. Modulation of Versican Synthesis in a Cell Culture

The effect of Ac-SEQ ID NO: 3-$NH_2$ peptide (synthesized in accordance with examples 1-3 and 5) on versican production was evaluated in vitro using human dermal fibroblasts (hereinafter, HDFa).

Briefly, HDFa cells were seeded in 96-well plates at $1 \times 10^4$ cells/well in fibroblasts growth media and maintained for 24 hours at standard culture conditions (37° C., 95% humidity, 5% $CO_2$). After the aforementioned incubation, medium was removed and new medium containing the non-cytotoxic concentrations of Ac-SEQ ID NO: 3-$NH_2$ peptide of: 0.01 mg/ml, 0.05 mg/ml and 0.1 mg/ml was added and incubated for 24 hours. 0.1 µM retinoic acid was included as positive control for versican stimulation and untreated cells were included as basal control. Cell culture media and cell lysate were collected from all wells at the end of the experiment and stored at −80° C. Ex-novo synthesis of versican was measured by means of sandwich ELISA following manufacturer's instructions.

Figure 2:
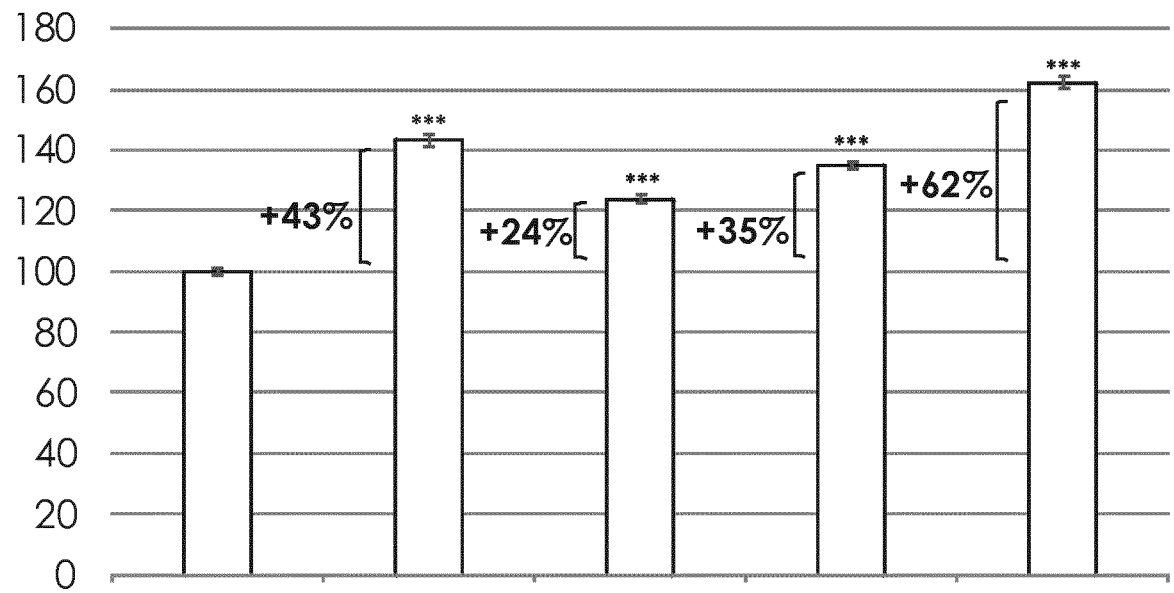
FIG. 2 shows the modulation of versican synthesis by Ac-SEQ ID NO: 3-$NH_2$. This is shown by means of the quantity of versican (secreted and intracellular) in the tested sample in comparison with the quantity of versican in the basal control (untreated cells), wherein the quantity of versican in the basal control is set to 100% and then the comparison with the rest of the samples is performed. Columns from left to right in the x-axis refer to: basal control, sample treated with 0.1 µM retinoic acid (positive control) and samples treated with different concentrations of Ac-SEQ ID NO: 3-$NH_2$ (0.01 mg/ml, 0.05 mg/ml and 0.1 mg/ml, respectively). The y axis shows the percentage of versican synthesis with regard to the basal control.

The results obtained are shown in FIG. 2.

As noted above, retinoic acid was used as positive control for the induction of the synthesis of versican.

As can be readily seen in FIG. 2, all the concentrations tested showed a significant increase in versican synthesis when compared with the basal control. Said increase in versican synthesis followed a dose response curve (increase in versican synthesis of 24%, 35% and 62% when compared to basal control at a concentration of 0.01 mg/ml, 0.05 mg/ml and 0.10 mg/ml of peptide, respectively), reaching values greater than those of retinoic acid at the highest concentration tested (this is, 0.10 mg/ml).

Example 9. Modulation of Tropoelastin Synthesis in a Cell Culture

The potential effect of Ac-SEQ ID NO: 3-$NH_2$ peptide (synthesized in accordance with examples 1-3 and 5) on tropoelastin synthesis was evaluated in vitro using HDFa.

HDFa were put in culture at a density of $1 \times 10^4$ cells/well in 96-well plates and incubated for 24 hours with non-cytotoxic increasing concentrations of Ac-SEQ ID NO: 3-$NH_2$ peptide (0.01 mg/ml, 0.05 mg/ml, 0.1 mg/ml and 0.5 mg/ml). Untreated cells were included as basal control. At the end of the monitored experimental time cell culture media and cell lysates were extracted from all wells and stored at −80° C. Ex-novo synthesis of tropoelastin was measured by means of sandwich ELISA following manufacturer's instructions.

Figure 3:
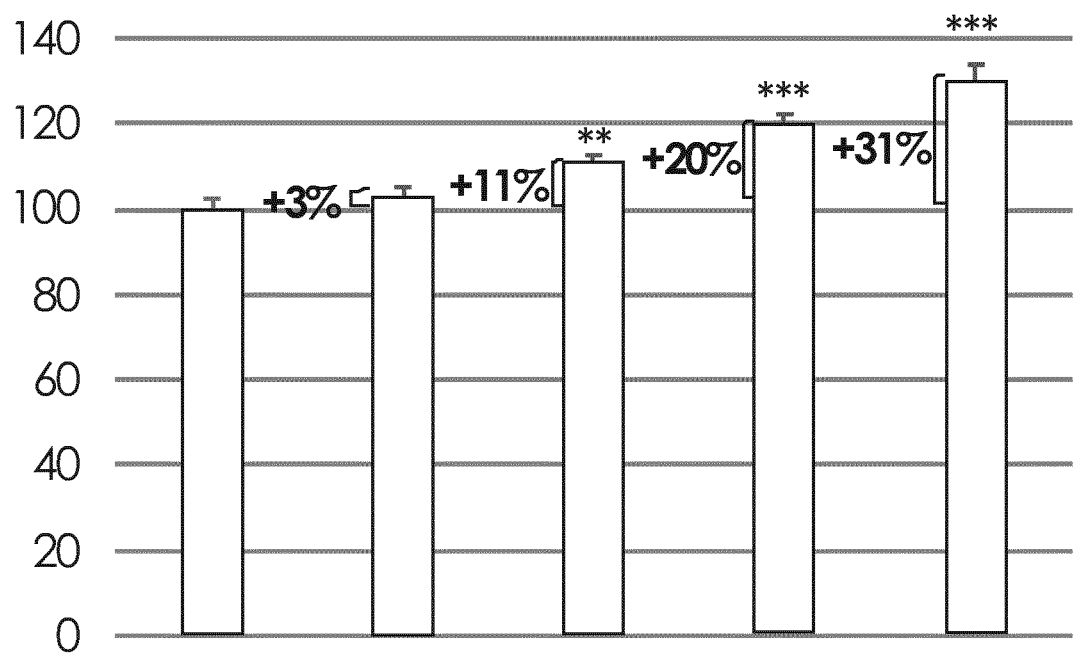
FIG. 3 shows the modulation of tropoelastin synthesis by Ac-SEQ ID NO: 3-$NH_2$. This is shown by means of the quantity of tropoelastin (secreted and intracellular) in the tested sample in comparison with the quantity of tropoelastin in the basal control (untreated cells), wherein the quantity of tropoelastin in the basal control is set as 100% and then the comparison with the rest of the samples is performed. Columns from left to right in the x-axis refer to: basal control and samples treated with different concentrations of Ac-SEQ ID NO: 3-$NH_2$ (0.01 mg/ml, 0.05 mg/ml, 0.1 mg/ml and 0.5 mg/ml, respectively). The y axis shows the percentage of tropoelastin synthesis with regard to the basal control.

The results of this experiment appear summarized in FIG. 3, where it can be seen that all the concentrations tested of the peptide Ac-SEQ ID NO: 3-$NH_2$ increased the synthesis of tropoelastin when compared with the basal control. Similarly, as for the synthesis of versican, the above-mentioned increase followed a dose response curve (increase in tropoelastin synthesis of 3%, 11%, 20% and 31% when compared to basal control at a concentration of 0.01 mg/ml, 0.05 mg/ml, 0.10 mg/ml and 0.50 mg/ml of peptide, respectively).

Example 10. Modulation of Fibrilin-1 Synthesis in a Cell Culture

Modulation of fibrilin-1 synthesis by Ac-SEQ ID NO: 3-$NH_2$ peptide (synthesized in accordance with examples 1-3 and 5) was evaluated in vitro using HDFa.

HDFa were seeded in 96-well plates at a density of $1 \times 10^4$ cells/well and they were put in contact with three non-cytotoxic concentrations of Ac-SEQ ID NO: 3-N $H_2$ peptide: 0.01 mg/ml, 0.05 mg/ml and 0.1 mg/ml for 48 hours. Untreated cells were included as basal control. At the end of the monitored experiment, cell culture media were extracted from all wells and stored at −80° C. Modulation on fibrilin-1 levels was analyzed by means of sandwich ELISA following manufacturer's instructions.

Figure 4:
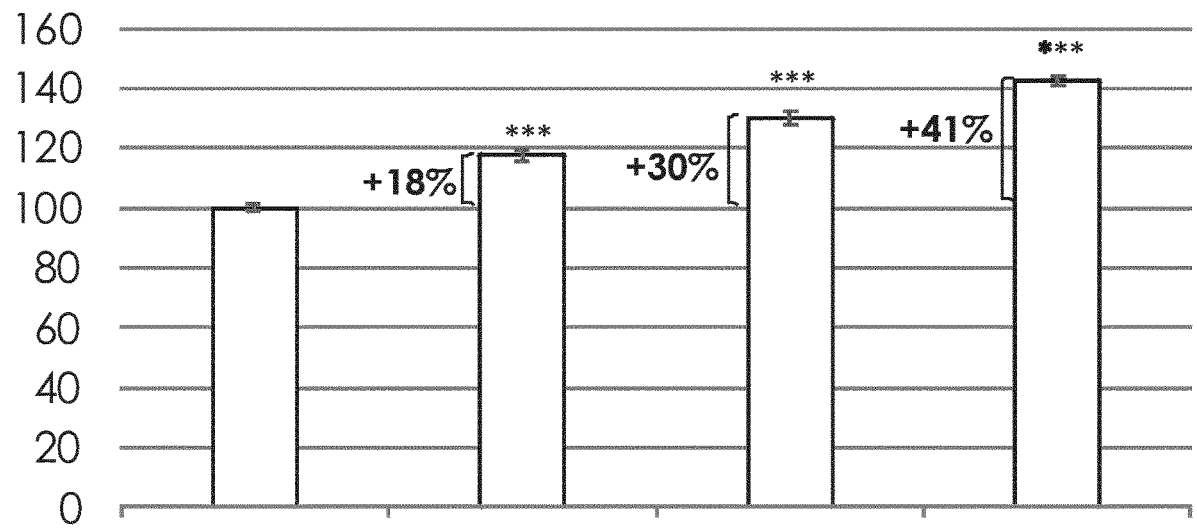
FIG. 4 shows the modulation of fibrillin-1 synthesis by Ac-SEQ ID NO: 3-N $H_2$. This is shown by means of the quantity of secreted fibrillin-1 in the tested sample in comparison with the quantity of fibrillin-1 in the basal control (untreated cells), wherein the quantity of fibrillin-1 in the basal control is set as 100% and then the comparison with the rest of the samples is performed. Columns from left to right in the x-axis refer to: basal control and samples treated with different concentrations of Ac-SEQ ID NO: 3-$NH_2$ (0.01 mg/ml, 0.05 mg/ml and 0.1 mg/ml, respectively). The y axis shows the percentage of fibrillin-1 synthesis with regard to the basal control.

The results of this experiment appear summarized in FIG. 4, were it can be seen that peptide Ac-SEQ ID NO: 3-$NH_2$ at all the concentrations tested, increased the synthesis of fibrilin-1 when compared to the basal control. Similarly, to the effect seen in the synthesis of versican and tropoelastin, the above-mentioned increase followed also a dose response curve (increase in fibrillin-1 synthesis of 18%, 30% and 41% when compared to basal control at a concentration of 0.01 mg/ml, 0.05 mg/ml and 0.10 mg/ml of peptide, respectively).

Example 11. Modulation of Hyaluronic Acid Synthesis in a Cell Culture

Modulation of Hyaluronic acid production by Ac-SEQ ID NO: 3-$NH_2$ peptide (synthesized in accordance with examples 1-3 and 5) on HDFa was evaluated in vitro.

Briefly, HDFa were seeded in 96-well plates at a density of $1 \times 10^4$ cells/well and, then, incubated with non-cytotoxic concentrations of Ac-SEQ ID NO: 3-$NH_2$ peptide, this is 0.01 mg/ml, 0.05 mg/ml, 0.1 mg/ml and 0.5 mg/ml, for 48 hours. 0.1 µM retinoic acid was included as positive control and untreated cells were included as basal control. At the end of the experiment, cell culture media were extracted from all wells and stored at −80° C. Ex-novo synthesis of hyaluronic acid was measured by means of competitive ELISA following manufacturer's instructions.

Figure 5:
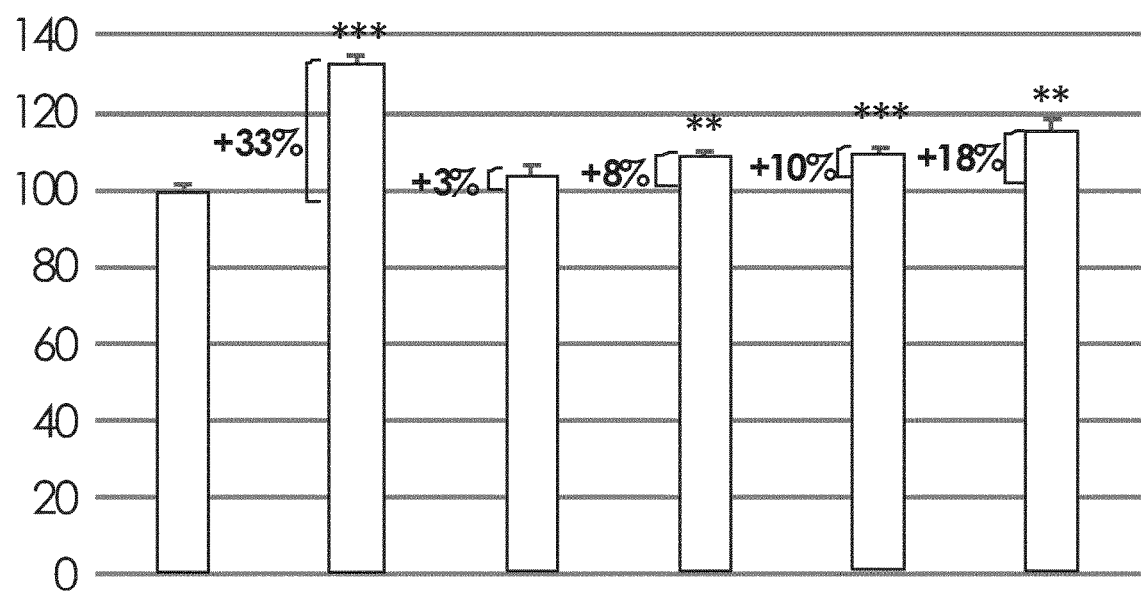
FIG. 5 shows the modulation of hyaluronic acid synthesis by Ac-SEQ ID NO: 3-$NH_2$. This is shown by means of the quantity of secreted hyaluronic acid in the tested sample in comparison with the quantity of hyaluronic acid in the basal control (untreated cells), wherein the quantity of hyaluronic acid in the basal control is set as 100% and then the comparison with the rest of the samples is performed. Columns from left to right in the x-axis refer to: basal control, positive control (sample treated with 0.1 µM retinoic acid) and samples treated with different concentrations of Ac-SEQ ID NO: 3-$NH_2$ (0.01 mg/ml, 0.05 mg/ml, 0.1 mg/ml and 0.5 mg/ml, respectively). The y axis shows the percentage of hyaluronic acid synthesis with regard to the basal control.

FIG. 5 shows the results obtained in this experiment for the modulation of hyaluronic acid synthesis by Ac-SEQ ID NO: 3-$NH_2$ peptide in vitro and in comparison with the basal control. Ac-SEQ ID NO: 3-N $H_2$ peptide induced a dose response increase of 3%, 8%, 10% and 18% in hyaluronic acid production, which is statistically significant in the three higher concentrations.

Example 12. Gene Expression Modulation in Cell Culture

Modulation of gene expression by Ac-SEQ ID NO: 3-$NH_2$ peptide (synthesized in accordance with examples 1-3 and 5) on HDFa was evaluated in vitro.

Briefly, HDFa cells were seeded in duplicate in 6-well plates at a density of $4 \times 10^5$ cells/well and they were maintained at standard culture conditions (37° C., 95% humidity, 5% $CO_2$) for 24 hours. Then, cells were treated with Ac-SEQ ID NO: 3-$NH_2$ peptide at the non-cytotoxic concentration of 0.05 and 0.1 mg/ml for additional 6 hours. Untreated cells were used as basal control. Cells were then lysed for RNA extraction with a RNA purification commercial kit following manufacturer instructions (RNeasy mini kit—Qiagen, Netherlands). RNA was then quantified by nanodrop, adjusted in concentration and processed for retrotranscription to cDNA using a commercially available kit (High-Capacity cDNA Reverse Transcription kit—Thermofisher Scientific, USA). Resulting cDNA was used to perform a RTqPCR (Real Time Quantitative Polymerase Chain Reaction) using taqman technology and a panel of probes designed to target specific genes related to extracellular matrix components and structure.

Figure 6:
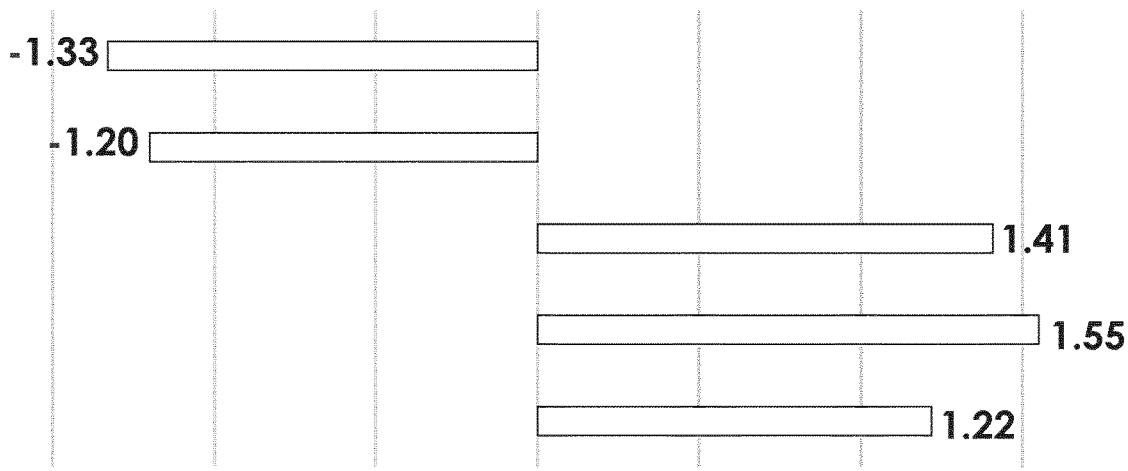
FIG. 6 shows the effect of Ac-SEQ ID NO: 3-$NH_2$ peptide on the gene expression profile of HDFa cells after 6-hour treatment with a peptide concentration of 0.05 mg/ml (for Fibrillin-1 and Versican) and 0.1 mg/ml (for Fibronectin 1 and metalloproteinases 1 and 3). Changes in gene expression levels are represented as a positive or negative fold-change with regard to the basal control (untreated cells). Bars from top to bottom in the y axis refer to: Metalloproteinase-1

The results of this example appear summarized in FIG. 6. Said figure shows that Ac-SEQ ID NO: 3-$NH_2$ peptide induces a downregulation of metalloproteinases 1 and 3, which are involved in the extracellular matrix degradation, with a fold change of −1.33 and −1.20, respectively. Also, Fibronectin 1, Fibrillin 1 and Versican, which are components of the extracellular matrix, are upregulated, with a fold change of 1.41, 1.55 and 1.22, respectively.

All the above experiments show that the peptides of the present invention exert an important activity towards both, maintaining the integrity of the extracellular matrix (by inhibiting the elastase activity and downregulating the expression of metalloproteinases at a genetic level) and producing extracellular matrix related components, for example, tropoelastin, versican, fibrillin-1 and hyaluronic acid, both at the genetic and at the protein level. Therefore, the above results show the usefulness of the peptides of the present invention in the field of cosmetics as firming agents which can be used in anti-aging products.

Example 13. Modulation of Versican Synthesis on Human Skin Explants

The effect of Ac-SEQ ID NO: 3-$NH_2$ peptide (synthesized in accordance with examples 1-3 and 5) on versican production was evaluated on human skin explants from a 46 years-old Caucasian female donor.

Briefly, skin explants were obtained from a volunteer donor undergoing a plastic surgery procedure. Skin excess was donated for the present study. Skin explants were treated with a cosmetic formulation containing 1% (m/v) from a stock at 0.05% (m/v) of Ac-SEQ ID NO: 3-$NH_2$ (effective final concentration of Ac-SEQ ID NO: 3-$NH_2$, 0.005 mg/ml). On days 0, 2, 4 and 7, the tested product was topically applied on the basis of 2 µl per $cm^2$ of skin explant and spread using a small spatula. The non-treated explants did not receive any treatment, except the renewal of half the culture medium (this is, 1 ml) on days 2, 4 and 7.

On day 9, 3 explants from each condition were collected and fixed in a buffered formalin solution. After fixation for 24 hours in buffered formalin, samples were dehydrated and impregnated and embedded in paraffin. 5-µm-thick sections were made using a Leica RM 2125 Minot-type microtome, and the sections were mounted on Superfrost® histological glass slides. The microscopical observations were performed using a Leica DMLB or Olympus BX43 microscope. Pictures were digitized with a numeric DP72 Olympus camera with CellD storing software.

Versican immunostaining was performed with a polyclonal anti-versican antibody (OriGene) diluted at 1/1000 in PBS-BSA 0.3% (m/v)-Tween 20 at 0.05% (v/v) for 1 h at room temperature, amplified using a biotin/streptavidin system (RTU, Kit vector) and revealed by VIP, a substrate of peroxidase (Vector). The immunostaining was performed using an automated slide-processing system (Dako, AutostainerPlus). The staining was assessed by microscopical observation and image analysis.

The results obtained are shown in FIG. 7.

As can be readily seen in FIG. 7, 0.005 mg/ml of Ac-SEQ ID NO: 3-N $H_2$ showed a significant increase in skin surface occupied by versican protein when compared with the non-treated explants (the increase in surface occupied by versican protein was of 29% when compared to basal control).

Example 14. Modulation of Fibrilin-1 Synthesis on Human Skin Explants

The effect of Ac-SEQ ID NO: 3-$NH_2$ peptide (synthesized in accordance with examples 1-3 and 5) on fibrillin-1 production was evaluated on human skin explants from a 46 years-old Caucasian female donor.

Briefly, skin explants were treated with a cosmetic formulation containing 1% (m/v) from a stock at 0.05% (m/v) of Ac-SEQ ID NO: 3-N $H_2$ (effective final concentration of Ac-SEQ ID NO: 3-N $H_2$, 0.005 mg/ml). On days 0, 2, 4 and 7, the tested product was topically applied on the basis of 2 µl per $cm^2$ of skin explant and spread using a small spatula.

The non-treated explants did not receive any treatment, except the renewal of half the culture medium (this is, 1 ml) on days 2, 4 and 7.

On day 9, 3 explants from each condition were collected and frozen at −80° C. The frozen samples were cut into 7-µm-thick sections using a Leica CM 3050 cryostat. Sections were then mounted on Superfrost® plus silanized glass slides. The microscopical observations were performed using a Leica DMLB or Olympus BX43 microscope. Pictures were digitized with a numeric DP72 Olympus camera with CellD storing software.

Fibrillin-1 immunostaining was realized on frozen sections with a monoclonal anti-fibrillin-1 antibody (Novus biologicals) diluted at 1/500 in PBS-BSA 0.3% (m/v)-Tween 20 at 0.05% (v/v) for 1 h at room temperature, amplified using a biotin/streptavidin system (RTU, Kit vector) and revealed by FITC (Invitrogen). The nuclei were counterstained using propidium iodide. The immunostaining was performed using an automated slide-processing system (Dako, AutostainerPlus). The staining was assessed by microscopical observation and image analysis.

The results obtained are shown in FIG. 8.

As can be readily seen in FIG. 8, 0.005 mg/ml of Ac-SEQ ID NO: 3-N $H_2$ showed a significant increase in skin surface occupied by fibrillin-1 protein when compared with the non-treated explants (the increase in surface occupied by fibrillin-1 protein was of 24% when compared to basal control).

Example 15 Clinical Evaluation of Skin Firmness and Antiaging Efficacy on Female Volunteers The effect of Ac-SEQ ID NO: 3-$NH_2$ peptide (synthesized in accordance with examples 1-3 and 5) on facial skin firmness was evaluated on 22 Caucasian female volunteers.

Briefly, volunteers applied a cosmetic formulation with 3% (m/v) from a stock at 0.05% (m/v) of Ac-SEQ ID NO: 3-$NH_2$ (effective final concentration of Ac-SEQ ID NO: 3-$NH_2$, 0.015 mg/ml) or without (placebo). The application regime was of two times per day during 56 days, on early morning and before bedtime. Cosmetic formulations were applied on either half of clean face in order to compare the effect of placebo and the active on the same volunteer.

On days 0, 7, 14 and 56, a Dynaskin device was used on each volunteer in order to measure the firmness quality of the skin according to three parameters: volume ($mm^3$), area ($mm^2$) and depth (mm). Dynaskin uses an air beam projection onto the cheek area causing a deformation of the skin. This deformation magnitude is measured by means of a specific software collecting data of the above three parameters for each volunteer and on each hemiface.

A decrease of any of the three parameters within the days of treatment indicated an increase of firmness on the face, hence an antiaging benefit.

The results obtained are shown in FIG. 9.

As can be readily seen in FIGS. 9 (A) to 9 (C), 0.015 mg/ml of Ac-SEQ ID NO: 3-$NH_2$ in a cosmetic formulation, showed decreases of either volume, area and/or depth on the region of facial skin studied in all studied times when compared to initial time (the decrease in any or all of these three parameters shows an increase in skin firmness and/or a facelift effect). As much as 20% decrease volume, 7% decrease area and 14.5% decrease depth was seen after 56 days of treatment (in the whole group treated with the cosmetic formulation comprising the peptide of the present invention; said percentages are even higher if only the responsive volunteers are considered).

The invention claimed is:

1. A peptide of formula (I):

their cosmetically acceptable isomers, salts, solvates and/or derivatives and mixtures thereof, wherein:

X is Ala;
$AA_1$ is Leu;
$AA_2$ is His;
$AA_3$ is Lys;
$AA_4$ is Val;
$AA_5$ is Lys;
Y is Val;
n and m are selected independently of each other from 0 and 1;
$R_1$ is selected from the group consisting of substituted or unsubstituted non-cyclic aliphatic, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO— wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3 to 10 members, and substituted or unsubstituted heteroarylalkyl of 2 to 24 carbon atoms and 1 to 3 atoms other than carbon and an alkyl chain of 1 to 6 carbon atoms and
$R_2$ is selected from the group consisting of —$NR_3R_4$—, —$OR_3$ and —$SR_3$—, wherein $R_3$ and $R_4$ are independently selected from H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl.

2. The peptide, in accordance with claim 1, wherein the amino acids are L-amino acids.

3. The peptide, in accordance with claim 1, wherein m is 0 and n is 1.

4. The peptide, in accordance with claim 1, wherein $R_1$ is acetyl or myristoyl.

5. The peptide, in accordance with claim 1, wherein $R_2$ is $NH_2$.

6. The peptide, in accordance with claim 1, wherein the peptide of formula (1) is:

$R_1$-Leu-His-Lys-Val-Lys-Val-$R_2$ ($R_1$-SEQ ID NO: 2-$R_2$); or $R_1$-Ala-Leu-His-Lys-Val-Lys-$R_2$ ($R_1$-SEQ ID NO: 3-$R_2$).

7. The peptide, in accordance with claim 6, wherein the peptide of formula (1) is:

Myristoyl-Leu-His-Lys-Val-Lys-Val-$NH_2$ (Myristoyl-SEQ ID NO: 2-$NH_2$); or

Ac-Ala-Leu-His-Lys-Val-Lys-NH2 (Ac-SEQ ID NO: 3-$NH_2$).

8. A cosmetic composition comprising the peptide in accordance with claim 1.

9. A method for delaying and/or reducing the signs of skin aging in a subject in need thereof, comprising administering peptide in accordance with claim 1.

10. A method for skin firming in a subject in need thereof, comprising administering the peptide in accordance with claim 1.

11. A method for delaying and/or reducing the signs of skin aging in a subject in need thereof comprising administering the cosmetic composition in accordance with claim 8.

12. A method for skin firming in a subject in need thereof comprising administering the cosmetic composition in accordance with claim 8.

* * * * *

SEQUENCE LISTING

```
<160> NUMBER OF SEQ ID NOS: 3

<210> SEQ ID NO 1
<211> LENGTH: 3396
<212> TYPE: PRT
<213> ORGANISM: Homo sapiens
<220> FEATURE:
<223> OTHER INFORMATION: Versican

<400> SEQUENCE: 1

Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
            20                  25                  30

Arg Gly Ser Leu Ser Gly Lys Val Ser Leu Pro Cys His Phe Ser Thr
        35                  40                  45

Met Pro Thr Leu Pro Pro Ser Tyr Asn Thr Ser Glu Phe Leu Arg Ile
    50                  55                  60

Lys Trp Ser Lys Ile Glu Val Asp Lys Asn Gly Lys Asp Leu Lys Glu
65                  70                  75                  80

Thr Thr Val Leu Val Ala Gln Asn Gly Asn Ile Lys Ile Gly Gln Asp
                85                  90                  95

Tyr Lys Gly Arg Val Ser Val Pro Thr His Pro Glu Ala Val Gly Asp
                100                 105                 110

Ala Ser Leu Thr Val Val Lys Leu Leu Ala Ser Asp Ala Gly Leu Tyr
            115                 120                 125
```

```
Arg Cys Asp Val Met Tyr Gly Ile Glu Asp Thr Gln Asp Thr Val Ser
130                 135                 140

Leu Thr Val Asp Gly Val Val Phe His Tyr Arg Ala Ala Thr Ser Arg
145                 150                 155                 160

Tyr Thr Leu Asn Phe Glu Ala Ala Gln Lys Ala Cys Leu Asp Val Gly
                165                 170                 175

Ala Val Ile Ala Thr Pro Glu Gln Leu Phe Ala Ala Tyr Glu Asp Gly
                180                 185                 190

Phe Glu Gln Cys Asp Ala Gly Trp Leu Ala Asp Gln Thr Val Arg Tyr
            195                 200                 205

Pro Ile Arg Ala Pro Arg Val Gly Cys Tyr Gly Asp Lys Met Gly Lys
210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Ala Lys Glu Cys Glu Asn
                260                 265                 270

Gln Asp Ala Arg Leu Ala Thr Val Gly Glu Leu Gln Ala Ala Trp Arg
            275                 280                 285

Asn Gly Phe Asp Gln Cys Asp Tyr Gly Trp Leu Ser Asp Ala Ser Val
290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Gly Phe Pro Pro
                325                 330                 335

Pro Asp Ser Arg Phe Asp Ala Tyr Cys Phe Lys Pro Lys Glu Ala Thr
                340                 345                 350

Thr Ile Asp Leu Ser Ile Leu Ala Glu Thr Ala Ser Pro Ser Leu Ser
                355                 360                 365

Lys Glu Pro Gln Met Val Ser Asp Arg Thr Thr Pro Ile Ile Pro Leu
370                 375                 380

Val Asp Glu Leu Pro Val Ile Pro Thr Glu Phe Pro Pro Val Gly Asn
385                 390                 395                 400

Ile Val Ser Phe Glu Gln Lys Ala Thr Val Gln Pro Gln Ala Ile Thr
                405                 410                 415

Asp Ser Leu Ala Thr Lys Leu Pro Thr Pro Thr Gly Ser Thr Lys Lys
                420                 425                 430

Pro Trp Asp Met Asp Asp Tyr Ser Pro Ser Ala Ser Gly Pro Leu Gly
                435                 440                 445

Lys Leu Asp Ile Ser Glu Ile Lys Glu Glu Val Leu Gln Ser Thr Thr
450                 455                 460

Gly Val Ser His Tyr Ala Thr Asp Ser Trp Asp Gly Val Val Glu Asp
465                 470                 475                 480

Lys Gln Thr Gln Glu Ser Val Thr Gln Ile Glu Gln Ile Glu Val Gly
                485                 490                 495

Pro Leu Val Thr Ser Met Glu Ile Leu Lys His Ile Pro Ser Lys Glu
                500                 505                 510

Phe Pro Val Thr Glu Thr Pro Leu Val Thr Ala Arg Met Ile Leu Glu
                515                 520                 525

Ser Lys Thr Glu Lys Lys Met Val Ser Thr Val Ser Glu Leu Val Thr
530                 535                 540

Thr Gly His Tyr Gly Phe Thr Leu Gly Glu Glu Asp Asp Glu Asp Arg
```

```
                545                 550                 555                 560
          Thr Leu Thr Val Gly Ser Asp Glu Ser Thr Leu Ile Phe Asp Gln Ile
                      565                 570                 575

Pro Glu Val Ile Thr Val Ser Lys Thr Ser Glu Asp Thr Ile His Thr
                      580                 585                 590

His Leu Glu Asp Leu Glu Ser Val Ser Ala Ser Thr Thr Val Ser Pro
                      595                 600                 605

Leu Ile Met Pro Asp Asn Asn Gly Ser Ser Met Asp Asp Trp Glu Glu
                      610                 615                 620

Arg Gln Thr Ser Gly Arg Ile Thr Glu Glu Phe Leu Gly Lys Tyr Leu
          625                 630                 635                 640

Ser Thr Thr Pro Phe Pro Ser Gln His Arg Thr Glu Ile Glu Leu Phe
                          645                 650                 655

Pro Tyr Ser Gly Asp Lys Ile Leu Val Glu Gly Ile Ser Thr Val Ile
                      660                 665                 670

Tyr Pro Ser Leu Gln Thr Glu Met Thr His Arg Arg Glu Arg Thr Glu
                      675                 680                 685

Thr Leu Ile Pro Glu Met Arg Thr Asp Thr Tyr Thr Asp Glu Ile Gln
                      690                 695                 700

Glu Glu Ile Thr Lys Ser Pro Phe Met Gly Lys Thr Glu Glu Glu Val
          705                 710                 715                 720

Phe Ser Gly Met Lys Leu Ser Thr Ser Leu Ser Glu Pro Ile His Val
                          725                 730                 735

Thr Glu Ser Ser Val Glu Met Thr Lys Ser Phe Asp Phe Pro Thr Leu
                      740                 745                 750

Ile Thr Lys Leu Ser Ala Glu Pro Thr Glu Val Arg Asp Met Glu Glu
                      755                 760                 765

Asp Phe Thr Ala Thr Pro Gly Thr Thr Lys Tyr Asp Glu Asn Ile Thr
                      770                 775                 780

Thr Val Leu Leu Ala His Gly Thr Leu Ser Val Glu Ala Ala Thr Val
          785                 790                 795                 800

Ser Lys Trp Ser Trp Asp Glu Asp Asn Thr Thr Ser Lys Pro Leu Glu
                          805                 810                 815

Ser Thr Glu Pro Ser Ala Ser Ser Lys Leu Pro Ala Leu Leu Thr
                      820                 825                 830

Thr Val Gly Met Asn Gly Lys Asp Lys Asp Ile Pro Ser Phe Thr Glu
                      835                 840                 845

Asp Gly Ala Asp Glu Phe Thr Leu Ile Pro Asp Ser Thr Gln Lys Gln
          850                 855                 860

Leu Glu Glu Val Thr Asp Glu Asp Ile Ala Ala His Gly Lys Phe Thr
          865                 870                 875                 880

Ile Arg Phe Gln Pro Thr Thr Ser Thr Gly Ile Ala Glu Lys Ser Thr
                          885                 890                 895

Leu Arg Asp Ser Thr Thr Glu Glu Lys Val Pro Pro Ile Thr Ser Thr
                      900                 905                 910

Glu Gly Gln Val Tyr Ala Thr Met Glu Gly Ser Ala Leu Gly Glu Val
                      915                 920                 925

Glu Asp Val Asp Leu Ser Lys Pro Val Ser Thr Val Pro Gln Phe Ala
                      930                 935                 940

His Thr Ser Glu Val Glu Gly Leu Ala Phe Val Ser Tyr Ser Ser Thr
          945                 950                 955                 960

Gln Glu Pro Thr Thr Tyr Val Asp Ser Ser His Thr Ile Pro Leu Ser
                      965                 970                 975
```

```
Val Ile Pro Lys Thr Asp Trp Gly Val Leu Val Pro Ser Val Pro Ser
            980                 985                 990

Glu Asp Glu Val Leu Gly Glu Pro Ser Gln Asp Ile Leu Val Ile Asp
        995                1000                1005

Gln Thr Arg Leu Glu Ala Thr Ile Ser Pro Gly Thr Met Arg Thr Thr
       1010                1015                1020

Lys Ile Thr Glu Gly Thr Thr Gln Glu Phe Pro Trp Lys Glu Gln
1025                1030                1035                1040

Thr Ala Glu Lys Pro Val Pro Ala Leu Ser Ser Thr Ala Trp Thr Pro
               1045                1050                1055

Lys Glu Ala Val Thr Pro Leu Asp Glu Gln Glu Gly Asp Gly Ser Ala
               1060                1065                1070

Tyr Thr Val Ser Glu Asp Glu Leu Leu Thr Gly Ser Glu Arg Val Pro
           1075                1080                1085

Val Leu Glu Thr Thr Pro Val Gly Lys Ile Asp His Ser Val Ser Tyr
           1090                1095                1100

Pro Pro Gly Ala Val Thr Glu His Lys Val Lys Thr Asp Glu Val Val
1105                1110                1115                1120

Thr Leu Thr Pro Arg Ile Gly Pro Lys Val Ser Leu Ser Pro Gly Pro
                1125                1130                1135

Glu Gln Lys Tyr Glu Thr Glu Gly Ser Ser Thr Thr Gly Phe Thr Ser
                1140                1145                1150

Ser Leu Ser Pro Phe Ser Thr His Ile Thr Gln Leu Met Glu Glu Thr
               1155                1160                1165

Thr Thr Glu Lys Thr Ser Leu Glu Asp Ile Asp Leu Gly Ser Gly Leu
               1170                1175                1180

Phe Glu Lys Pro Lys Ala Thr Glu Leu Ile Glu Phe Ser Thr Ile Lys
1185                1190                1195                1200

Val Thr Val Pro Ser Asp Ile Thr Thr Ala Phe Ser Ser Val Asp Arg
                1205                1210                1215

Leu His Thr Thr Ser Ala Phe Lys Pro Ser Ser Ala Ile Thr Lys Lys
               1220                1225                1230

Pro Pro Leu Ile Asp Arg Glu Pro Gly Glu Glu Thr Thr Ser Asp Met
                1235                1240                1245

Val Ile Ile Gly Glu Ser Thr Ser His Val Pro Pro Thr Thr Leu Glu
                1250                1255                1260

Asp Ile Val Ala Lys Glu Thr Glu Thr Asp Ile Asp Arg Glu Tyr Phe
1265                1270                1275                1280

Thr Thr Ser Ser Pro Pro Ala Thr Gln Pro Thr Arg Pro Pro Thr Val
               1285                1290                1295

Glu Asp Lys Glu Ala Phe Gly Pro Gln Ala Leu Ser Thr Pro Gln Pro
               1300                1305                1310

Pro Ala Ser Thr Lys Phe His Pro Asp Ile Asn Val Tyr Ile Ile Glu
               1315                1320                1325

Val Arg Glu Asn Lys Thr Gly Arg Met Ser Asp Leu Ser Val Ile Gly
               1330                1335                1340

His Pro Ile Asp Ser Glu Ser Lys Glu Asp Glu Pro Cys Ser Glu Glu
1345                1350                1355                1360

Thr Asp Pro Val His Asp Leu Met Ala Glu Ile Leu Pro Glu Phe Pro
                1365                1370                1375

Asp Ile Ile Glu Ile Asp Leu Tyr His Ser Glu Glu Asn Glu Glu Glu
                1380                1385                1390
```

-continued

Glu Glu Glu Cys Ala Asn Ala Thr Asp Val Thr Thr Thr Pro Ser Val
            1395                1400                1405

Gln Tyr Ile Asn Gly Lys His Leu Val Thr Thr Val Pro Lys Asp Pro
    1410                1415                1420

Glu Ala Ala Glu Ala Arg Arg Gly Gln Phe Glu Ser Val Ala Pro Ser
1425                1430                1435                1440

Gln Asn Phe Ser Asp Ser Ser Glu Ser Asp Thr His Pro Phe Val Ile
            1445                1450                1455

Ala Lys Thr Glu Leu Ser Thr Ala Val Gln Pro Asn Glu Ser Thr Glu
            1460                1465                1470

Thr Thr Glu Ser Leu Glu Val Thr Trp Lys Pro Glu Thr Tyr Pro Glu
            1475                1480                1485

Thr Ser Glu His Phe Ser Gly Gly Glu Pro Asp Val Phe Pro Thr Val
            1490                1495                1500

Pro Phe His Glu Glu Phe Glu Ser Gly Thr Ala Lys Lys Gly Ala Glu
1505                1510                1515                1520

Ser Val Thr Glu Arg Asp Thr Glu Val Gly His Gln Ala His Glu His
            1525                1530                1535

Thr Glu Pro Val Ser Leu Phe Pro Glu Glu Ser Ser Gly Glu Ile Ala
            1540                1545                1550

Ile Asp Gln Glu Ser Gln Lys Ile Ala Phe Ala Arg Ala Thr Glu Val
            1555                1560                1565

Thr Phe Gly Glu Glu Val Glu Lys Ser Thr Ser Val Thr Tyr Thr Pro
    1570                1575                1580

Thr Ile Val Pro Ser Ser Ala Ser Ala Tyr Val Ser Glu Glu Ala
1585                1590                1595                1600

Val Thr Leu Ile Gly Asn Pro Trp Pro Asp Asp Leu Leu Ser Thr Lys
            1605                1610                1615

Glu Ser Trp Val Glu Ala Thr Pro Arg Gln Val Val Glu Leu Ser Gly
            1620                1625                1630

Ser Ser Ser Ile Pro Ile Thr Glu Gly Ser Gly Glu Ala Glu Glu Asp
            1635                1640                1645

Glu Asp Thr Met Phe Thr Met Val Thr Asp Leu Ser Gln Arg Asn Thr
    1650                1655                1660

Thr Asp Thr Leu Ile Thr Leu Asp Thr Ser Arg Ile Ile Thr Glu Ser
1665                1670                1675                1680

Phe Phe Glu Val Pro Ala Thr Thr Ile Tyr Pro Val Ser Glu Gln Pro
            1685                1690                1695

Ser Ala Lys Val Val Pro Thr Lys Phe Val Ser Glu Thr Asp Thr Ser
            1700                1705                1710

Glu Trp Ile Ser Ser Thr Thr Val Glu Glu Lys Lys Arg Lys Glu Glu
            1715                1720                1725

Glu Gly Thr Thr Gly Thr Ala Ser Thr Phe Glu Val Tyr Ser Ser Thr
            1730                1735                1740

Gln Arg Ser Asp Gln Leu Ile Leu Pro Phe Glu Leu Glu Ser Pro Asn
1745                1750                1755                1760

Val Ala Thr Ser Ser Asp Ser Gly Thr Arg Lys Ser Phe Met Ser Leu
            1765                1770                1775

Thr Thr Pro Thr Gln Ser Glu Arg Glu Met Thr Asp Ser Thr Pro Val
            1780                1785                1790

Phe Thr Glu Thr Asn Thr Leu Glu Asn Leu Gly Ala Gln Thr Thr Glu
            1795                1800                1805

His Ser Ser Ile His Gln Pro Gly Val Gln Glu Gly Leu Thr Thr Leu

```
                1810                1815                1820

Pro Arg Ser Pro Ala Ser Val Phe Met Glu Gln Gly Ser Gly Glu Ala
1825                1830                1835                1840

Ala Ala Asp Pro Glu Thr Thr Thr Val Ser Ser Phe Ser Leu Asn Val
                1845                1850                1855

Glu Tyr Ala Ile Gln Ala Glu Lys Glu Val Ala Gly Thr Leu Ser Pro
                1860                1865                1870

His Val Glu Thr Thr Phe Ser Thr Glu Pro Thr Gly Leu Val Leu Ser
                1875                1880                1885

Thr Val Met Asp Arg Val Val Ala Glu Asn Ile Thr Gln Thr Ser Arg
                1890                1895                1900

Glu Ile Val Ile Ser Glu Arg Leu Gly Glu Pro Asn Tyr Gly Ala Glu
1905                1910                1915                1920

Ile Arg Gly Phe Ser Thr Gly Phe Pro Leu Glu Glu Asp Phe Ser Gly
                1925                1930                1935

Asp Phe Arg Glu Tyr Ser Thr Val Ser His Pro Ile Ala Lys Glu Glu
                1940                1945                1950

Thr Val Met Met Glu Gly Ser Gly Asp Ala Ala Phe Arg Asp Thr Gln
                1955                1960                1965

Thr Ser Pro Ser Thr Val Pro Thr Ser Val His Ile Ser His Ile Ser
                1970                1975                1980

Asp Ser Glu Gly Pro Ser Ser Thr Met Val Ser Thr Ser Ala Phe Pro
1985                1990                1995                2000

Trp Glu Glu Phe Thr Ser Ser Ala Glu Gly Ser Gly Glu Gln Leu Val
                2005                2010                2015

Thr Val Ser Ser Ser Val Val Pro Val Leu Pro Ser Ala Val Gln Lys
                2020                2025                2030

Phe Ser Gly Thr Ala Ser Ser Ile Ile Asp Glu Gly Leu Gly Glu Val
                2035                2040                2045

Gly Thr Val Asn Glu Ile Asp Arg Arg Ser Thr Ile Leu Pro Thr Ala
                2050                2055                2060

Glu Val Glu Gly Thr Lys Ala Pro Val Glu Lys Glu Glu Val Lys Val
2065                2070                2075                2080

Ser Gly Thr Val Ser Thr Asn Phe Pro Gln Thr Ile Glu Pro Ala Lys
                2085                2090                2095

Leu Trp Ser Arg Gln Glu Val Asn Pro Val Arg Gln Glu Ile Glu Ser
                2100                2105                2110

Glu Thr Thr Ser Glu Glu Gln Ile Gln Glu Glu Lys Ser Phe Glu Ser
                2115                2120                2125

Pro Gln Asn Ser Pro Ala Thr Glu Gln Thr Ile Phe Asp Ser Gln Thr
2130                2135                2140

Phe Thr Glu Thr Glu Leu Lys Thr Thr Asp Tyr Ser Val Leu Thr Thr
2145                2150                2155                2160

Lys Lys Thr Tyr Ser Asp Asp Lys Glu Met Lys Glu Glu Asp Thr Ser
                2165                2170                2175

Leu Val Asn Met Ser Thr Pro Asp Pro Asp Ala Asn Gly Leu Glu Ser
                2180                2185                2190

Tyr Thr Thr Leu Pro Glu Ala Thr Glu Lys Ser His Phe Phe Leu Ala
                2195                2200                2205

Thr Ala Leu Val Thr Glu Ser Ile Pro Ala Glu His Val Val Thr Asp
                2210                2215                2220

Ser Pro Ile Lys Lys Glu Glu Ser Thr Lys His Phe Pro Lys Gly Met
2225                2230                2235                2240
```

-continued

```
Arg Pro Thr Ile Gln Glu Ser Asp Thr Glu Leu Leu Phe Ser Gly Leu
            2245                2250                2255

Gly Ser Gly Glu Glu Val Leu Pro Thr Leu Pro Thr Glu Ser Val Asn
        2260                2265                2270

Phe Thr Glu Val Glu Gln Ile Asn Asn Thr Leu Tyr Pro His Thr Ser
        2275                2280                2285

Gln Val Glu Ser Thr Ser Ser Asp Lys Ile Glu Asp Phe Asn Arg Met
        2290                2295                2300

Glu Asn Val Ala Lys Glu Val Gly Pro Leu Val Ser Gln Thr Asp Ile
2305                2310                2315                2320

Phe Glu Gly Ser Gly Ser Val Thr Ser Thr Thr Leu Ile Glu Ile Leu
            2325                2330                2335

Ser Asp Thr Gly Ala Glu Gly Pro Thr Val Ala Pro Leu Pro Phe Ser
            2340                2345                2350

Thr Asp Ile Gly His Pro Gln Asn Gln Thr Val Arg Trp Ala Glu Glu
            2355                2360                2365

Ile Gln Thr Ser Arg Pro Gln Thr Ile Thr Glu Gln Asp Ser Asn Lys
            2370                2375                2380

Asn Ser Ser Thr Ala Glu Ile Asn Glu Thr Thr Thr Ser Ser Thr Asp
2385                2390                2395                2400

Phe Leu Ala Arg Ala Tyr Gly Phe Glu Met Ala Lys Glu Phe Val Thr
            2405                2410                2415

Ser Ala Pro Lys Pro Ser Asp Leu Tyr Tyr Glu Pro Ser Gly Glu Gly
            2420                2425                2430

Ser Gly Glu Val Asp Ile Val Asp Ser Phe His Thr Ser Ala Thr Thr
            2435                2440                2445

Gln Ala Thr Arg Gln Glu Ser Ser Thr Thr Phe Val Ser Asp Gly Ser
            2450                2455                2460

Leu Glu Lys His Pro Glu Val Pro Ser Ala Lys Ala Val Thr Ala Asp
2465                2470                2475                2480

Gly Phe Pro Thr Val Ser Val Met Leu Pro Leu His Ser Glu Gln Asn
            2485                2490                2495

Lys Ser Ser Pro Asp Pro Thr Ser Thr Leu Ser Asn Thr Val Ser Tyr
            2500                2505                2510

Glu Arg Ser Thr Asp Gly Ser Phe Gln Asp Arg Phe Arg Glu Phe Glu
            2515                2520                2525

Asp Ser Thr Leu Lys Pro Asn Arg Lys Lys Pro Thr Glu Asn Ile Ile
            2530                2535                2540

Ile Asp Leu Asp Lys Glu Asp Lys Asp Leu Ile Leu Thr Ile Thr Glu
2545                2550                2555                2560

Ser Thr Ile Leu Glu Ile Leu Pro Glu Leu Thr Ser Asp Lys Asn Thr
            2565                2570                2575

Ile Ile Asp Ile Asp His Thr Lys Pro Val Tyr Glu Asp Ile Leu Gly
            2580                2585                2590

Met Gln Thr Asp Ile Asp Thr Glu Val Pro Ser Glu Pro His Asp Ser
            2595                2600                2605

Asn Asp Glu Ser Asn Asp Asp Ser Thr Gln Val Gln Glu Ile Tyr Glu
            2610                2615                2620

Ala Ala Val Asn Leu Ser Leu Thr Glu Glu Thr Phe Glu Gly Ser Ala
2625                2630                2635                2640

Asp Val Leu Ala Ser Tyr Thr Gln Ala Thr His Asp Glu Ser Met Thr
            2645                2650                2655
```

-continued

Tyr Glu Asp Arg Ser Gln Leu Asp His Met Gly Phe His Phe Thr Thr
         2660                2665                2670

Gly Ile Pro Ala Pro Ser Thr Glu Thr Glu Leu Asp Val Leu Leu Pro
    2675                2680                2685

Thr Ala Thr Ser Leu Pro Ile Pro Arg Lys Ser Ala Thr Val Ile Pro
2690                2695                2700

Glu Ile Glu Gly Ile Lys Ala Glu Ala Lys Ala Leu Asp Asp Met Phe
2705                2710                2715                2720

Glu Ser Ser Thr Leu Ser Asp Gly Gln Ala Ile Ala Asp Gln Ser Glu
            2725                2730                2735

Ile Ile Pro Thr Leu Gly Gln Phe Glu Arg Thr Gln Glu Glu Tyr Glu
        2740                2745                2750

Asp Lys Lys His Ala Gly Pro Ser Phe Gln Pro Glu Phe Ser Ser Gly
    2755                2760                2765

Ala Glu Glu Ala Leu Val Asp His Thr Pro Tyr Leu Ser Ile Ala Thr
    2770                2775                2780

Thr His Leu Met Asp Gln Ser Val Thr Glu Val Pro Asp Val Met Glu
2785                2790                2795                2800

Gly Ser Asn Pro Pro Tyr Tyr Thr Asp Thr Thr Leu Ala Val Ser Thr
            2805                2810                2815

Phe Ala Lys Leu Ser Ser Gln Thr Pro Ser Ser Pro Leu Thr Ile Tyr
            2820                2825                2830

Ser Gly Ser Glu Ala Ser Gly His Thr Glu Ile Pro Gln Pro Ser Ala
        2835                2840                2845

Leu Pro Gly Ile Asp Val Gly Ser Ser Val Met Ser Pro Gln Asp Ser
2850                2855                2860

Phe Lys Glu Ile His Val Asn Ile Glu Ala Thr Phe Lys Pro Ser Ser
2865                2870                2875                2880

Glu Glu Tyr Leu His Ile Thr Glu Pro Pro Ser Leu Ser Pro Asp Thr
            2885                2890                2895

Lys Leu Glu Pro Ser Glu Asp Asp Gly Lys Pro Glu Leu Leu Glu Glu
        2900                2905                2910

Met Glu Ala Ser Pro Thr Glu Leu Ile Ala Val Glu Gly Thr Glu Ile
    2915                2920                2925

Leu Gln Asp Phe Gln Asn Lys Thr Asp Gly Gln Val Ser Gly Glu Ala
2930                2935                2940

Ile Lys Met Phe Pro Thr Ile Lys Thr Pro Glu Ala Gly Thr Val Ile
2945                2950                2955                2960

Thr Thr Ala Asp Glu Ile Glu Leu Glu Gly Ala Thr Gln Trp Pro His
            2965                2970                2975

Ser Thr Ser Ala Ser Ala Thr Tyr Gly Val Glu Ala Gly Val Val Pro
        2980                2985                2990

Trp Leu Ser Pro Gln Thr Ser Glu Arg Pro Thr Leu Ser Ser Ser Pro
    2995                3000                3005

Glu Ile Asn Pro Glu Thr Gln Ala Ala Leu Ile Arg Gly Gln Asp Ser
    3010                3015                3020

Thr Ile Ala Ala Ser Glu Gln Gln Val Ala Ala Arg Ile Leu Asp Ser
3025                3030                3035                3040

Asn Asp Gln Ala Thr Val Asn Pro Val Glu Phe Asn Thr Glu Val Ala
            3045                3050                3055

Thr Pro Pro Phe Ser Leu Leu Glu Thr Ser Asn Glu Thr Asp Phe Leu
        3060                3065                3070

Ile Gly Ile Asn Glu Glu Ser Val Glu Gly Thr Ala Ile Tyr Leu Pro

```
                3075              3080              3085
Gly Pro Asp Arg Cys Lys Met Asn Pro Cys Leu Asn Gly Gly Thr Cys
    3090              3095              3100

Tyr Pro Thr Glu Thr Ser Tyr Val Cys Thr Cys Val Pro Gly Tyr Ser
3105              3110              3115              3120

Gly Asp Gln Cys Glu Leu Asp Phe Asp Glu Cys His Ser Asn Pro Cys
                3125              3130              3135

Arg Asn Gly Ala Thr Cys Val Asp Gly Phe Asn Thr Phe Arg Cys Leu
            3140              3145              3150

Cys Leu Pro Ser Tyr Val Gly Ala Leu Cys Glu Gln Asp Thr Glu Thr
        3155              3160              3165

Cys Asp Tyr Gly Trp His Lys Phe Gln Gly Gln Cys Tyr Lys Tyr Phe
    3170              3175              3180

Ala His Arg Arg Thr Trp Asp Ala Ala Glu Arg Glu Cys Arg Leu Gln
3185              3190              3195              3200

Gly Ala His Leu Thr Ser Ile Leu Ser His Glu Glu Gln Met Phe Val
                3205              3210              3215

Asn Arg Val Gly His Asp Tyr Gln Trp Ile Gly Leu Asn Asp Lys Met
            3220              3225              3230

Phe Glu His Asp Phe Arg Trp Thr Asp Gly Ser Thr Leu Gln Tyr Glu
        3235              3240              3245

Asn Trp Arg Pro Asn Gln Pro Asp Ser Phe Phe Ser Ala Gly Glu Asp
    3250              3255              3260

Cys Val Val Ile Ile Trp His Glu Asn Gly Gln Trp Asn Asp Val Pro
3265              3270              3275              3280

Cys Asn Tyr His Leu Thr Tyr Thr Cys Lys Lys Gly Thr Val Ala Cys
                3285              3290              3295

Gly Gln Pro Pro Val Val Glu Asn Ala Lys Thr Phe Gly Lys Met Lys
            3300              3305              3310

Pro Arg Tyr Glu Ile Asn Ser Leu Ile Arg Tyr His Cys Lys Asp Gly
        3315              3320              3325

Phe Ile Gln Arg His Leu Pro Thr Ile Arg Cys Leu Gly Asn Gly Arg
    3330              3335              3340

Trp Ala Ile Pro Lys Ile Thr Cys Met Asn Pro Ser Ala Tyr Gln Arg
3345              3350              3355              3360

Thr Tyr Ser Met Lys Tyr Phe Lys Asn Ser Ser Ser Ala Lys Asp Asn
                3365              3370              3375

Ser Ile Asn Thr Ser Lys His Asp His Arg Trp Ser Arg Trp Gln
            3380              3385              3390

Glu Ser Arg Arg
        3395

<210> SEQ ID NO 2
<211> LENGTH: 6
<212> TYPE: PRT
<213> ORGANISM: Artificial Sequence
<220> FEATURE:
<223> OTHER INFORMATION: Artificially synthesized peptide

<400> SEQUENCE: 2

Leu His Lys Val Lys Val
1               5

<210> SEQ ID NO 3
<211> LENGTH: 6
<212> TYPE: PRT
```

```
<213> ORGANISM: Artificial Sequence
<220> FEATURE:
<223> OTHER INFORMATION: Artificially synthesized peptide

<400> SEQUENCE: 3

Ala Leu His Lys Val Lys
1               5
```